(12) United States Patent
Hutvagner et al.

(10) Patent No.: US 8,598,143 B2
(45) Date of Patent: *Dec. 3, 2013

(54) SEQUENCE-SPECIFIC INHIBITION OF SMALL RNA FUNCTION

(75) Inventors: Gyorgy Hutvagner, Worcester, MA (US); Phillip D. Zamore, Northboro, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/273,673

(22) Filed: Nov. 19, 2008

(65) Prior Publication Data

US 2009/0083873 A1 Mar. 26, 2009

Related U.S. Application Data

(62) Division of application No. 10/998,364, filed on Nov. 26, 2004.

(60) Provisional application No. 60/525,474, filed on Nov. 26, 2003, provisional application No. 60/543,796, filed on Feb. 10, 2004.

(51) Int. Cl.
*A01N 43/04* (2006.01)

(52) U.S. Cl.
USPC .............................. 514/55; 435/455; 424/93.2

(58) Field of Classification Search
None
See application file for complete search history.

(56) References Cited

U.S. PATENT DOCUMENTS

| | | | |
|---|---|---|---|
| 5,898,031 | A | 4/1999 | Crooke |
| 6,107,094 | A | 8/2000 | Crooke |
| 6,673,611 | B2 | 1/2004 | Thompson et al. |
| 6,737,512 | B2 | 5/2004 | Wu et al. |
| 7,217,807 | B2 | 5/2007 | Bentwich |
| 7,232,806 | B2 | 6/2007 | Tuschl et al. |
| 7,307,067 | B2 | 12/2007 | Sarnow et al. |
| 7,365,058 | B2 | 4/2008 | Stoffel et al. |
| 7,432,249 | B2 | 10/2008 | Crooke |
| 7,432,250 | B2 | 10/2008 | Crooke |
| 7,582,744 | B2 | 9/2009 | Manoharan et al. |
| 7,585,969 | B2 | 9/2009 | Stoffel et al. |
| 7,683,036 | B2 | 3/2010 | Esau et al. |
| 2002/0164601 | A1 | 11/2002 | Wu et al. |
| 2002/0165189 | A1 | 11/2002 | Crooke |
| 2003/0044941 | A1 | 3/2003 | Crooke |
| 2003/0096286 | A1 | 5/2003 | Crooke |
| 2003/0096287 | A1 | 5/2003 | Crooke |
| 2003/0096784 | A1 | 5/2003 | Crooke |
| 2003/0119777 | A1 | 6/2003 | Crooke |
| 2004/0053411 | A1 | 3/2004 | Cullen et al. |
| 2004/0146902 | A1 | 7/2004 | Ecker et al. |
| 2004/0147022 | A1 | 7/2004 | Baker et al. |
| 2004/0147023 | A1 | 7/2004 | Baker et al. |
| 2004/0147470 | A1 | 7/2004 | Manoharan et al. |
| 2004/0161777 | A1 | 8/2004 | Baker et al. |
| 2004/0161844 | A1 | 8/2004 | Baker et al. |
| 2004/0171028 | A1 | 9/2004 | Baker et al. |
| 2004/0171029 | A1 | 9/2004 | Prakash et al. |
| 2004/0171030 | A1 | 9/2004 | Baker et al. |
| 2004/0171031 | A1 | 9/2004 | Baker et al. |
| 2004/0171032 | A1 | 9/2004 | Baker et al. |
| 2004/0171033 | A1 | 9/2004 | Baker et al. |
| 2004/0191773 | A1 | 9/2004 | Crooke |
| 2004/0203024 | A1 | 10/2004 | Baker et al. |
| 2004/0219515 | A1* | 11/2004 | Bentwich ......................... 435/5 |
| 2004/0259247 | A1* | 12/2004 | Tuschl et al. ................. 435/375 |
| 2005/0037370 | A1 | 2/2005 | Baker et al. |
| 2005/0037387 | A1 | 2/2005 | Ward |
| 2005/0042647 | A1 | 2/2005 | Baker et al. |
| 2005/0053976 | A1 | 3/2005 | Baker et al. |
| 2005/0059005 | A1* | 3/2005 | Tuschl et al. ...................... 435/6 |
| 2005/0118605 | A9 | 6/2005 | Baker et al. |
| 2005/0119470 | A1 | 6/2005 | Manoharan et al. |
| 2005/0171041 | A1 | 8/2005 | Kowalik et al. |
| 2005/0182005 | A1* | 8/2005 | Tuschl et al. .................... 514/44 |
| 2005/0227934 | A1 | 10/2005 | Stoffel et al. |
| 2005/0261218 | A1 | 11/2005 | Esau et al. |
| 2006/0058266 | A1 | 3/2006 | Manoharan et al. |

(Continued)

FOREIGN PATENT DOCUMENTS

| | | |
|---|---|---|
| CA | 2533701 A1 | 2/2005 |
| WO | WO-94/01550 A1 | 1/1994 |

(Continued)

OTHER PUBLICATIONS

Lagos-Quintana et al. (2001) "Identification of novel genes coding for small expressed RNAs" Science 294 :853-858.*
Bennet et al. "Antisense oligonucleotides as a tool for gene functionalization and target validation" Biochimica et Biophysica Acta 1489:19-30.*
Kurreck (Apr. 2003) "Antisense technologies: Improvement through novel chemical modifcations" Eur. J. Biochem. 270:1628-1644.*
Schmitz et al. "Effect of 2"-O-methyl antisense ORNs on expression of thymidylate synthase in human colon cancer RKO cells" (2001) Nucleic Acids Research 29:415-422.*
Bartel (2004) Cell 116:281-297.*
Bartel et al., 2003, Plant Physiol., 132:709-717.*
Freund, et al. (2001) Inhibtion of HIV-1 Replication in Vitro and in Human Infected Cells by Modified Antisense Oligonucleotides Targeting the tRNAlys3/RNA Initiation Complex, Antisense & Nucleic Acid Drug Development, V.11:301-15.*

(Continued)

*Primary Examiner* — Jennifer McDonald
(74) *Attorney, Agent, or Firm* — Nelson Mullins Riley & Scarborough LLP; Debra J. Milasincic, Esq.

(57) ABSTRACT

The present invention relates to the discovery of a method for inhibiting RNA silencing in a target sequence-specific manner. RNA silencing requires a set of conserved cellular factors to suppress expression of gene-encoded polypeptide. The invention provides compositions for sequence-specific inactivation of the RISC component of the RNA silencing pathway, and methods of use thereof. The RISC inactivators of the present invention enable a variety of methods for identifying and characterizing miRNAs and siRNAs, RISC-associated factors, and agents capable of modulating RNA silencing. Therapeutic methods and compositions incorporating RISC inactivators and therapeutic agents identified through use of RISC inactivators are also featured.

13 Claims, 16 Drawing Sheets

(56) References Cited

U.S. PATENT DOCUMENTS

| | | | |
|---|---|---|---|
| 2006/0105360 | A1 | 5/2006 | Croce et al. |
| 2006/0241072 | A1 | 10/2006 | Baker |
| 2006/0252722 | A1 | 11/2006 | Lollo et al. |
| 2007/0027592 | A1 | 2/2007 | Tolkacz |
| 2007/0049547 | A1 | 3/2007 | Esau et al. |
| 2007/0123482 | A1 | 5/2007 | Stoffel et al. |
| 2007/0155682 | A1* | 7/2007 | Tiedge ............................ 514/44 |
| 2007/0213292 | A1 | 9/2007 | Stoffel et al. |
| 2007/0287179 | A1 | 12/2007 | Tuschl et al. |
| 2008/0119427 | A1 | 5/2008 | Bhat et al. |
| 2009/0043082 | A1 | 2/2009 | Stoffel et al. |
| 2009/0203893 | A1 | 8/2009 | Esau et al. |
| 2009/0261218 | A1 | 10/2009 | Dellach |
| 2009/0275729 | A1 | 11/2009 | Stoffel et al. |
| 2009/0286969 | A1 | 11/2009 | Esau et al. |
| 2009/0286973 | A1 | 11/2009 | Manoharan et al. |
| 2009/0291906 | A1 | 11/2009 | Esau et al. |
| 2009/0291907 | A1 | 11/2009 | Esau et al. |
| 2009/0298174 | A1 | 12/2009 | Esau et al. |
| 2009/0317907 | A1 | 12/2009 | Esau et al. |

FOREIGN PATENT DOCUMENTS

| | | | |
|---|---|---|---|
| WO | WO-9746570 | | 12/1997 |
| WO | WO-03/029459 | | 4/2003 |
| WO | WO 03/029459 | * | 4/2003 |
| WO | WO-03070904 | | 8/2003 |
| WO | 03/093441 | A2 | 11/2003 |
| WO | WO-2004/014933 | | 2/2004 |
| WO | WO-2004/076622 | A2 | 9/2004 |
| WO | WO-2005/001043 | | 1/2005 |
| WO | WO-2005013901 | | 2/2005 |
| WO | WO-2005/019433 | | 3/2005 |
| WO | WO-2005/042705 | | 5/2005 |
| WO | WO-2005/044976 | | 5/2005 |
| WO | WO-2005/079397 | A2 | 9/2005 |
| WO | WO-2005099770 | | 10/2005 |
| WO | WO-2006020768 | | 2/2006 |
| WO | WO-2007021896 | | 2/2007 |
| WO | WO-2007027775 | | 3/2007 |
| WO | WO-2007027894 | | 3/2007 |

OTHER PUBLICATIONS

Yekta, et al. (2004) MicroRNA-Directed Cleavage of HOXB8 mRNA. Science, v.304:594-6.*

Allerson, Charles R. et al, "Fully 2'-Modified Oligonucleotide Duplexes with Improved in Vitro Potency and Stability Compared to Unmodified Small Interfering RNA," *J. Med. Chem.*, vol. 48:901-904 (2005).

Amarzguioui, Mohammad et al, "Secondary structure prediction in vitro accessibility of mRNA as tools in the selection of target sites for ribozymes," *Nucleic Acids Research*, vol. 28(21):4113-4124 (2000).

Amarzguioui, Mohammed et al, "Tolerance for mutations and chemical modifications in a siRNA," *Nucleic Acids Research*, vol. 31(2):589-595 (2003).

Ambros, Victor et al., "MicroRNAs and Other Tiny Endogenous RNAs in *C. elegans*," *Current Biology*, vol. 13:807-818 (2003).

Aravin, Alexei A. et al., "The Small RNA Profile during *Drosophila melanogaster* Development," *Developmental Cell*, vol. 5:337-350 (2003).

Bernstein, Emily et al., "Role for a bidentate ribonuclease in the initiation step of RNA interference," *Nature*, vol. 409:363-366 (2001).

Billy, Eric et al., "Specific interference with gene expression induced by long, double-stranded RNA in mouse embryonal tetrocarcinoma cell lines," *PNAS*, vol. 98(25):14428-14433 (2001).

Boulmé, Florence et al, "Modified (PNA, 2'-O-methyl and phosphoramidate) anti-TAR antisense oligonucleotides as strong and specific inhibitors of in vitro HIV-1 reverse transcription," *Nucleic Acids Research*, vol. 26(23):5492-5500 (1998).

Boutla, Alexandra et al, "Developmental defects by antisense-mediated inactivation of micro-RNAs 2 and 13 in *Drosophila* and the identification of putative target genes," *Nucleic Acids Research*, vol. 31(17):4973-4980 (2003).

Boutla, Alexandra et al, "Short 5'-phosphorylated double-stranded RNAs induce RNA interference in *Drosophila*," *Current Biology*, vol. 11:1776-1780 (2001).

Brennecke, Julius et al., "*bantam* Encodes a Developmentally Regulated microRNA that Controls Cell Proliferation and Regulates the Proapoptotic Gene *hid* in Drosophila," *Cell*, vol. 113:25-36 (2003).

Bridge, Alan J. et al., "Induction of an interferon response by RNAi vectors in mammalian cells," *Nature Genetics*, vol. 34:263-264 (2003).

Brummelkamp, Thijn R. et al., "A System for Stable Expression of Short Interfering RNAs in Mammalian Cells," *Science*, vol. 296:550-553 (2002).

Cairns, M.J. et al, "Catalytic DNA: A Novel Tool for Gene Suppression," *Current Drug Targets*, vol. 3:269-279 (2002).

Caré, Alessandra et al., "MicroRNA-133 controls cardiac hypertrophy," *Nature Medicine*, vol. 13(5):613-618 (2007).

Catalanotto, Caterina et al., "Involvement of small RNAs and role of the *qde* genes in the gene silencing pathway in *Neurospora*," *Genes & Development*, vol. 16:790-795 (2002).

Caudy, Amy A. et al., "Fragile X-related protein and VIG associate with the RNA interference machinery," *Genes & Development*, vol. 16:2491-2496 (2002).

Chiu, Ya-Lin et al., "RNAi in Human Cells: Basic Structural and Functional Features of Small Interfering RNA," *Molecular Cell*, vol. 10:549-561 (2002).

Chiu, Ya-Lin et al, "siRNA function in RNAi: A chemical modification analysis," *RNA*, vol. 9:1034-1048 (2003).

Crow, John P. et al., "Decreased Zinc Affinity of Amyotrophic Lateral Sclerosis-Associated Superoxide Dismutase Mutants Leads to Enhanced Catalysis of Tyrosine Nitration by Peroxynitrite," *Journal of Neurochemistry*, vol. 69:1936-1944 (1997).

Cummins, Lendell L. et al, "Characterization of fully 2'-modified oligoribonucleotide hetero- and homoduplex hybridization and nuclease sensitivity," *Nucleic Acids Research*, vol. 23(11):2019-2024 (1995).

Czauderna, Frank et al, "Structural variations and stabilising modifications of synthetic siRNAs in mammalian cells," *Nucleic Acids Research*, vol. 31(11):2705-2716 (2003).

Dalmay, Tamas et al., "*SDE3* encodes an RNA helicase required for post-transcriptional gene silencing in *Arabidopsis*," *The EMBO Journal*, vol. 20(8):2069-2077 (2001).

Doench, John G. et al., "siRNAs can function as miRNAs," *Genes & Development*, vol. 17:438-442 (2003).

Doench, John G. et al, "Specificity of microRNA target selection in translational repression," *Genes & Development*, pp. 504-511 (2004).

Doi, Noboru et al., "Short-Interfering-RNA-Mediated Gene Silencing in Mammalian Cells Requires Dicer and elF2C Translation Initiation Factors," *Current Biology*, vol. 13:41-46 (2003).

Dölken, Lars et al., "Mouse Cytomegalovirus MicroRNAs Dominate the Cellular Small RNA Profile during Lytic Infection and Show Features of Prosttranscriptional Regulation," *Journal of Virology*, vol. 81(24):13771-13782 (2007).

Elbashir, Sayda M. et al, "Functional anatomy of siRNAs for mediating efficient RNAi in *Drosophila melanogaster* embryo lysate," *The EMBO Journal*, vol. 20(23):6877-6888 (2001).

Elbashir, Sayda M. et al., "RNA interference is mediated by 21- and 22-nucleotide RNAs," *Genes & Development*, vol. 15:188-200 (2001).

Elmén, Joacim et al, "Locked nucleic acid (LNA) mediated improvements in siRNA stability and functionality," *Nucleic Acids Research*, vol. 33(1):439-447 (2005).

Esau, Christine et al., "MicroRNA-143 Regulates Adipocyte Differentiation," *The Journal of Biological Chemistry*, vol. 279(50):52361-52365 (2004).

Esau, Christine et al., "miR-122 regulation of lipid metabolism revealed by in vivo antisense targeting," *Cell Metabolism*, vol. 3:87-98 (2006).

Esau, Christine C. et al., "Therapeutic potential for microRNAs," *Advanced Drug Delivery Reviews*, vol. 59:101-114 (2007).

Fire, Andrew et al., "Potent and specific genetic interference by double-stranded RNA in *Caenorhabditis elegans*," *Nature*, vol. 391:806-811 (1998).

(56) References Cited

OTHER PUBLICATIONS

Gewirtz, Alan M. et al, "Nucleic Acid Therapeutics: State of the Art and Future Prospects," *Blood*, vol. 92(3):712-736 (1998).
Gottwein, Eva et al., "A viral microRNA functions as an orthologue of cellular miR-155," *Nature*, vol. 450:1096-1099 (2007).
Grishok, Alla et al., "Genes and Mechanisms Related to RNA Interference Regulate Expression of the Small Temporal RNAs that Control *C. elegans* Developmental Timing," *Cell*, vol. 106:23-34 (2001).
Haley, Benjamin et al., "In vitro analysis of RNA interference in *Drosophila melanogaster*," *Methods*, vol. 30:330-336 (2003).
Hamilton, Andrew J. et al., "A Species of Small Antisense RNA in Posttranscriptional Gene Silencing in Plants," *Science*, vol. 286:950-952 (1999).
Hammond, Scott M. et al., "An RNA-directed nuclease mediates post-transcriptional gene silencing in *Drosophila* cells," *Nature*, vol. 404:293-296 (2000).
Hammond, Scott M. et al., "Post-Transcriptional Gene Silencing by Double-Stranded RNA," *Nature*, vol. 2:110-119 (2001).
Hutvágner, György et al, "A microRNA in a Multiple-Turnover RNAi Enzyme Complex," *Science*, vol. 297:2056-2060 (2002).
Hutvágner, György et al., "A Cellular Function for the RNA-Interference Enzyme Dicer in the Maturation of the *let-7* Small Temporal RNA," *Science*, vol. 293:834-838 (2001).
Hutvágner, György et al, "Sequence-Specific Inhibition of Small RNA Function," *PLOS Biology*, vol. 2(4):0465-0475 (2004).
Inoue, Hideo et al, "Synthesis and hybridization studies on two complementary nona(2'-O-methyl)ribonucleotides," *Nucleic Acids Research*, vol. 15(15):6131-6148 (1987).
Ishizuka, Akira et al., "A *Drosophila* fragile X protein interacts with components of RNAi and ribosomal proteins," *Genes & Development*, vol. 16:2497-2508 (2002).
Jackson, Aimee L. et al., "Expression profiling reveals off-target gene regulation by RNAi," *Nature Biotechnology*, vol. 21:635-637 (2003).
Jen, Kuang-Yu et al, "Suppression of Gene Expression by Targeted Disruption of Messenger RNA: Available Options and Current Strategies," *Stem Cells*, vol. 18:307-319 (2000).
Jopling, Catherine L. et al., "Modulation of Hepatitis C Virus RNA Abundance by a Liver-Specific MicroRNA," *Science*, vol. 309:1577-1581 (2005).
Kasschau, Kristin D. et al, "P1/HC-Pro, a Viral Suppressor of RNA Silencing, Interferes with *Arabidopsis* Development and miRNA Function," *Developmental Cell*, vol. 4:205-217 (2003).
Kennerdell, Jason R. et al., "RNAi is activated during *Drosophila* oocyte maturation in a manner dependent on *aubergine* and *spindle-E*," *Genes & Development*, vol. 16:1884-1889 (2002).
Ketting, René F. et al., "Dicer functions in RNA interference and in synthesis of small RNA involved in developmental timing in *C. elegans*," *Genes & Development*, vol. 15:2654-2659 (2001).
Khvorova, Anastasia et al., "Functional siRNAs and miRNAs Exhibit Strand Bias," *Cell*, vol. 115:209-216 (2003).
Kim, Joseph L. et al., "Hepatitis C virus NS3 RNA helicase domain with a bound oligonucleotide: the crystal structure provides insights into the mode of unwinding," *Structure*, vol. 6(1):89-100 (1998).
Knight, Scott W. et al., "A Role for the RNase III Enzyme DCR-1 in RNA Interference and Germ Line Development in *Caenorhabditis elegans*," *Science*, vol. 293:2269-2271 (2001).
Krützfeldt, Jan et al., "Silencing of microRNAs in vivo with 'antagomirs,'" *Nature*, vol. 438:685-689 (2005).
Krützfeldt, Jan et al., "Specificity, duplex degradation and subcellular localization of antagomirs," *Nucleic Acids Research*, vol. 35(9):2885-2892 (2007).
Lagos-Quintana, Mariana et al., "Identification of Novel Genes Coding for Small Expressed RNAs," *Science*, vol. 294:853-858 (2001).
Lagos-Quintana, Mariana et al., "Identification of Tissue-Specific MicroRNAs from Mouse," *Current Biology*, vol. 12:735-739 (2002).
Lagos-Quintana, Mariana et al., "New MicroRNAs from mouse and human," *RNA*, vol. 9:175-179 (2003).
Lau, Nelson C. et al., "An Abundant Class of Tiny RNAs with Probable Regulatory Roles in *Caenorhabditis elegans*," *Science*, vol. 294:858-862 (2001).
Lee, Rosalind C. et al., "An Extensive Class of Small RNAs in *Caenorhabditis elegans*," *Science*, vol. 294:862-864 (2001).
Lee, Rosalind C. et al., "The *C. elegans* Heterochronic Gene *lin-4* Encodes Small RNAs with Antisense Complementarity to *lin-14*," *Cell*, vol. 75:843-854 (1993).
Li, Qi-Jing et al., "miR-181a Is an Intrinsic Modulator of T Cell Sensitivity and Selection," *Cell*, vol. 129:147-161 (2007).
Lim, Lee P. et al., "The microRNAs of *Caenorhabditis elegans*," *Genes & Development*, vol. 17:991-1008 (2003).
Lim, Lee P. et al., "Vertebrate MicroRNA Genes," *Science*, vol. 299:1540 (2003).
Liu, Jidong et al, "Argonaute2 Is the Catalytic Engine of Mammalian RNAi," *Science*, vol. 305:1437-1441 (2004).
Majlessi, Mehrdad et al, "Advantages of 2'-O-methyl oligoribonucleotide probes for detecting RNA targets," *Nucleic Acids Research*, vol. 26(9):2224-2229 (1998).
Mallory, Allison C. et al., "A viral suppressor of RNA silencing differentially regulates the accumulation of short interfering RNAs and micro-RNAs in tobacco," *PNAS*, vol. 99(23):15228-15233 (2002).
Martinez, Javier et al, "Single-Stranded Antisense siRNAs Guide Target RNA Cleavage in RNAi," *Cell*, vol. 110:563-574 (2002).
Mathews, David H. et al., "Expanded Sequence Dependence on Thermodynamic Parameters Improves Prediction of RNA Secondary Structure," *J. Mol. Biol.*, vol. 288:911-940 (1999).
McManus, Michael T. et al., "Gene silencing using micro-RNA designed hairpins," *RNA*, vol. 8:842-850 (2002).
Meister, Gunter et al, "Sequence-specific inhibition of microRNA- and siRNA-induced RNA silencing," *RNA*, vol. 10:544-550 (2004).
Molenaar, C. et al, "Linear 2' O-Methyl RNA probes for the visualization of RNA in living cells," *Nucleic Acids Research*, vol. 29(17):1-9 (2001).
Mourelatos, Zissimos et al., "miRNPs: a novel class of ribonucleoproteins containing numerous microRNAs," *Genes & Development*, vol. 16:720-728 (2002).
Myers, Jason W. et al., "Recombinant Dicer efficiently converts large dsRNAs into siRNAs suitable for gene silencing," *Nature Biotechnology*, vol. 21:324-328 (2003).
Nykänen, Antti et al., "ATP Requirements and Small Interfering RNA Structure in the RNA Interference Pathway," *Cell*, vol. 107:309-321 (2001).
Opalinska, Joanna B. et al, "Nucleic-Acid Therapeutics: Basic Principles and Recent Applications," *Nature*, vol. 1:503-514 (2002).
Paddison, Patrick J. et al., "Short hairpin RNAs (shRNAs) induce sequence-specific silencing in mammalian cells," *Genes & Development*, vol. 16:948-958 (2002).
Paolella, Giovanni et al, "Nuclease resistant ribozymes and high catalytic activity," *The EMBO Journal*, vol. 11(5):1913-1919 (1992).
Park, Wonkeun et al., "Carpel Factory, a Dicer Homolog, and HEN1, a Novel Protein, Act in microRNA Metabolism in *Arabidopsis thaliana*," *Current Biology*, vol. 12:1484-1495 (2002).
Parrish, Susan et al, "Distinct roles for RDE-1 and RDE-4 during RNA interference in *Caenorhabditis elegans*," *RNA*, vol. 7:1397-1402 (2001).
Parrish, Susan et al, "Functional Anatomy of a dsRNA Trigger: Differential Requirement for the Two Trigger Strands in RNA Interference," *Molecular Cell*, vol. 6:1077-1087 (2000).
Pasquinelli, Amy E. et al., "Conservation of the sequence and temporal expression of *let-7* heterochronic regulatory RNA," *Nature*, vol. 408:86-89 (2000).
Paul, Cynthia P. et al., "Effective expression of small interfering RNA in human cells," *Nature Biotechnology*, vol. 20:505-508 (2002).
Pieken, Wolfgang A. et al, "Kinetic Characterization of Ribonuclease-Resistant 2'-Modified Hammerhead Ribozymes," *Science*, vol. 253:314-317 (1991).
Provost, Patrick et al., "Ribonuclease activity and RNA binding of recombinant human Dicer," *The EMBO Journal*, vol. 21(21):5864-5874 (2002).
Reinhart, Brenda J. et al., "MicroRNAs in plants," *Genes & Development*, vol. 16:1616-1626 (2002).
Reinhart, Brenda J. et al., "The 21-nucleotide *let-7* RNA regulates developmental timing in *Caenorhabditis elegans*," *Nature*, vol. 403:901-906 (2000).

(56) References Cited

OTHER PUBLICATIONS

Schwarz, et al., "Asymmetry in the Assembly of the RNAi Enzyme Complex," *Cell*, vol. 115:199-208 (2003).
Schwarz, Dianne S. et al., "Evidence that siRNAs Function as Guides, Not Primers, in the *Drosophila* and Human RNAi Pathways," *Molecular Cell*, vol. 10:537-548 (2002).
Sijen, Titia et al., "One the Role of RNA Amplification in dsRNA-Triggered Gene Silencing," *Cell*, vol. 107:465-476 (2001).
Song, Ji-Joon et al, "Crystal Structure of Argonaute and Its Implications for RISC Slicer Activity," *Science*, vol. 305:1434-1436 (2004).
Sontheimer, Erik J. et al, "Argonaute Journeys into the Heart of RISC," *Science*, vol. 305:1409-1410 (2004).
Sui, Guangchao et al., "A DNA vector-based RNAi technology to suppress gene expression in mammalian cells," *PNAS*, vol. 99(8):5515-5520 (2002).
Tabara, Hiroaki et al., "The dsRNA Binding Protein RDE-4 Interacts with RDE-1, DCR-1, and a DExH-Box Helicase to Direct RNAi in *C. elegans*," *Cell*, vol. 109:861-871 (2002).
Tang, Guiliang et al., "A biochemical framework for RNA silencing in plants," *Genes & Development*, vol. 17:49-63 (2003).
Tijsterman, Marcel et al., "RNA Helicase MUT-14-Dependent Gene Silencing Triggered in *C. elegans* by Short Antisense RNAs," *Science*, vol. 295:694-697 (2002).
Turner, Douglas H. et al., "Free Energy Increments for Hydrogen Bonds in Nucleic Acid Base Pairs," *J. Am. Chem. Soc.*, vol. 109:3783-3785 (1987).
Tuschl, Thomas et al., "Targeted mRNA degradation by double-stranded RNA in vitro," *Genes & Development*, vol. 13:3191-3197 (1999).
Velankar, Sameer S. et al., "Crystal Structures of Complexes of PcrA DNA Helicase with a DNA Substrate Indicate an Inchworm Mechanism," *Cell*, vol. 97:75-84 (1999).
Vickers, Timothy A. et al., "Efficient Reduction of Target RNAs by Small Interfering RNA and RNase H-dependent Antisense Agents," *The Journal of Biological Chemistry*, vol. 278(9):7108-7118 (2003).
Wu-Scharf, Dancia et al., "Transgene and Transposon Silencing in *Chlamydomonas reinhardtii* by a DEAH-Box RNA Helicase," *Science*, vol. 290:1159-1162 (2000).
Yu, Jenn-Yah et al., "RNA interference by expression of short-interfering RNAs and hairpin RNAs in mammalian cells," *PNAS*, vol. 99(9):6047-6052 (2002).
Zamore, Phillip D. et al., "RNAi: Double-Stranded RNA Directs the ATP-Dependent Cleavage of mRNA at 21 to 23 Nucleotide Intervals," *Cell*, vol. 101:25-33 (2000).
Zeng, Yan et al, "Both Natural and Designed Micro RNAs Can Inhibit the Expression on Cognate mRNAs When Expressed in Human Cells," *Molecular Cell*, vol. 9:1327-1333 (2002).
Zeng, Yan et al, "MicroRNAs and small interfering RNAs can inhibit mRNA expression by similar mechanisms," *PNAS*, vol. 100(17):9779-9784 (2003).
Zeng, Yan et al, "Sequence requirements for micro RNA processing and function in human cells," *RNA*, vol. 9:112-123 (2003).
Zhang, Haidi et al., "Human Dicer preferentially cleaves dsRNAs at their termini without a requirement for ATP," *The EMBO Journal*, vol. 21(21):5875-5885 (2002).
Zuker, Michael, "Mfold web server for nucleic acid folding and hybridization prediction," *Nucleic Acids Research*, vol. 31(13):3406-3415 (2003).
International Search Report for Application No. PCT/US04/39731, dated Mar. 8, 2006.
Bennett, C. Frank et al., "Antisense oligonucleotides as a tool for gene functionalization and target validation," Biochimica et Biophysica Acta, vol. 1489:19-30 (1999).
Kurreck, Jens, "Antisense technologies. Improvement through novel chemical modifications," Eur. J. Biochem., vol. 270:1628-1644 (2003).
Ambros, Victor, "microRNAs: Tiny Regulators with Great Potential," Cell, vol. 107:823-826 (2001).
Chen, Chang-Zheng et al., "MicroRNAs Modulate Hennatopoietic Lineage Differentiation," Science, vol. 303:83-86 (2004).
Elmń, Joacim et al., "Antagonism of microRNA-122 in mice by systemically administered LNA-antimiR leads to up-regulation of a large set of predicted target mRNAs in the liver," Nucleic Acids Research, vol. 36(4):1153-1162 (2008).
Elmén, Joacim et al., "LNA-mediated microRNA silencing in non-human primates," Nature, vol. 452:896-899 (2008).
Fuyuno, Ichiko et al., "Doubts over biochemist's data expose holes in Japanese fraud laws," Nature, vol. 439:514 (2006).
Fuyuno, Ichiko et al., "Further accusations rock Japanese RNA laboratory," Nature, vol. 440:720-721 (2006).
Fuyuno, Ichiko,"Lack of lab notes casts doubt on RNA researcher's results," Nature, vol. 437:461 (2005).
Grishok and Mello, "RNAi and Development References," Advances in Genetics, vol. 46:340-360 (2002).
Grosshans, Helge et al., "Micro-RNAs: small is plentiful," The Journal of Cell Biology, vol. 156(1):17-21 (2002).
He, Lin et al., "MicroRNAs: Small RNAs with a Big Role in Gene Regulation," Nature, vol. 5:522-531 (2004).
Kawasaki, Hiroaki et al., "Hes1 is a target of microRNA-23 during retinoic-acid-induced neuronal differentiation of NT2 cells," Nature, vol. 423:838-842 (2003) and retraction, Nature, vol. 426:100 (2003).
Lai, Eric C., "MicroRNAs are complementary to 3' UTR sequence motifs that mediate negative post-transcriptional regulation," Nature Genetics, vol. 30:363-364 (2002).
Lee, Yoontae et al., "MicroRNA maturation: stepwise processing and subcellular localization," The EMBO Journal, vol. 21(17):4663-4670 (2002).
Moss, Eric G., "MicroRNAs: Hidden in the Genome," Current Biology, vol. 12:R138-R140 (2002).
Moss, Eric G., "Non-coding RNAs: Lightning strikes twice," Current Biology, vol. 10:R436-R439 (2000).
Moss, Eric G., "RNA interference: It's a small RNA world," Current Biology, vol. 11:R772-R775 (2001).
Pasquinelli, Amy E. et al., "Control of Developmental Timing by MicroRNAs and Their Targets," Annu. Rev. Cell Dev., vol. 18:495-513 (2002).
Pasquinelli, Amy E. et al., "MicroRNAs: deviants no longer," Trends in Genetics, vol. 18(4):171-173 (2002).
Petri, Andreas et al., "MicroRNA Silencing in Primates: Towards Development of Novel Therapeutics," Cancer Res., vol. 69(2):393-395 (2009).
Riddihough, Guy, "The Other RNA World," Science, vol. 296:1259 (2002).
Schwarz, Dianne S. et al., "Why do miRNAs live in the miRNP?" Genes & Development, vol. 16:1025-1031 (2002).
Storz, Gisela, "An Expanding Universe of Noncoding RNAs," Science, vol. 296:1260-1262 (2002).
Thum, Thomas et al., "MicroRNA-21 contributes to myocardial disease by stimulating MAP kinase signalling in fibroblasts," Nature, vol. 456:980-984 (2008).
Würdinger, Thomas et al., "miR-296 Regulates Growth Factor Receptor Overexpression in Angiogenic Endothelial Cells," Cancer Cell, vol. 14:382-393 (2008).
Zamore, Phillip D., "Ancient Pathways Programmed by Small RNAs," Science, vol. 296:1265-1269 (2002).
Supplementary Partial European Search Report for Application No. 04812289.9, 3 pages, dated Mar. 6, 2013.

* cited by examiner

Exhibit B

FIG. 1A

```
sense 2'-O-Me oligo      3'-ccuguaagcuucauaaggcgcaugcacuac-Bi-5'
                                                            (SEQ ID NO: 2)
sense target          3'-...ccuguaagcuucauaaggcgcaugcacuacaag...-5'
                            ||||||||||||||||||||||||||||
                                                            (SEQ ID NO: 7)
siRNA                    5'-ucgaaguauuccgcuacgug-3' (anti-sense strand)
                            ||||||||||||||||||||
                                                            (SEQ ID NO: 8)
                         3'-aaagcuucauaaggcgcaugc-5' (sense strand)
                             ·|||||||||||||||||||
                                                            (SEQ ID NO: 9)
anti-sense target        5'-...ggacauuucgaaguauuccgcuacgugauguuc...-3'
                               ||||||||||||||||||||||||||||
                                                            (SEQ ID NO: 10)
anti-sense 2'-O-Me oligo 5'-Bi-acauuucgaaguauuccgcuacgugauguu-3'
                                                            (SEQ ID NO: 4)
```

Exhibit B

Exhibit B

2'-O-Me oligo    5'-ggacauuucgaaguauuccgcguacgugaug-3' (SEQ ID NO: 3)
                    ||||||||||||||||||||||||||||||
RNA target      3'-....ccuguaaagcuucauaaggcgcaugcacuacaagug....-5' (SEQ ID NO: 11)
                          ||||||||||||||||||||||||||||
siRNA              5'-ucgaaguauuccgcguacgug-3' (SEQ ID NO: 8)
                      ::::::::::::::::::::
                   3'-aaagcuucauaaggcgcaugc-5' (SEQ ID NO: 9)

RISC = 14.5 nM

IC50 = 303 ± 0.02 nM

```
2'-O-Me oligo    3'-guagugcaugcgccuuaugaagcuuuacagg-5'           (SEQ ID NO: 3)
RNA target       3'-...gcuccacuuguagugcaugcgccuuaugaagcuuuacagg...-5'  (SEQ ID NO: 12)
                        ∙ ||||||||||||||||||||||
siRNA            5'-uguacgcggaauacuucgaaa-3'                     (SEQ ID NO: 13)
                    ∙ ∙ ∙∙∙∙∙∙∙∙∙∙∙∙∙∙∙∙∙
                 3'-gugcaugcgccuuaugaagcu-5'                     (SEQ ID NO: 8)
```

RISC = 16.8 nM

IC50 = 8.2 ± 0.73 nM

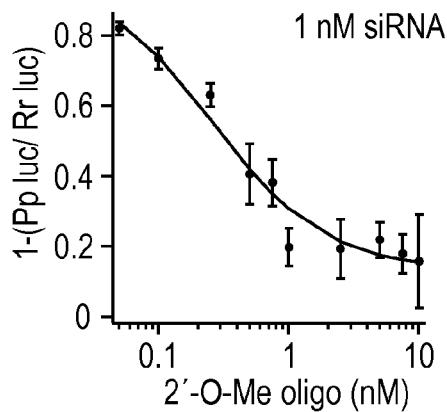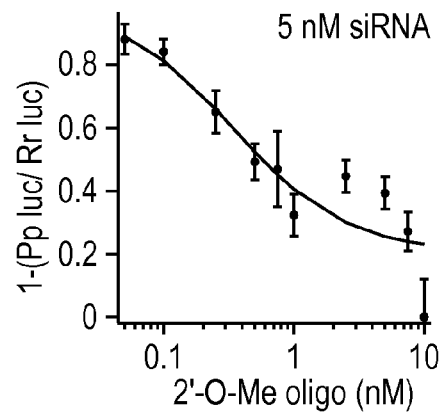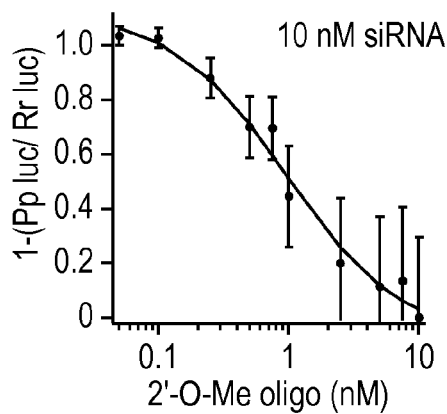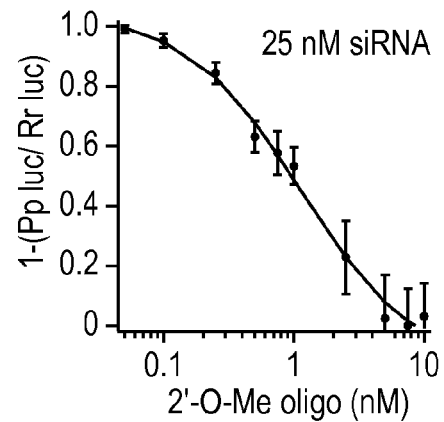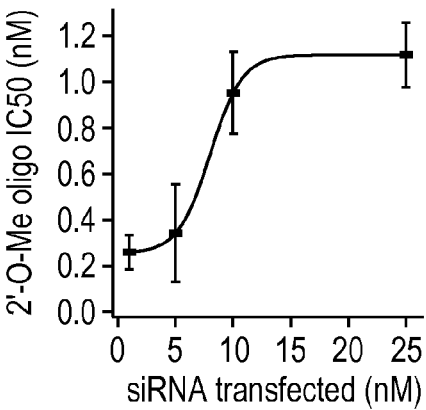

FIG. 8A
| | Gene Symbol | FoldChange | AdjP-value |
|---|---|---|---|
| *let-7* inhibition | | | |
| | HMGA2 | 3.4 | 1.59E-07 |
| | DICER1 | 2.6 | 0.047 |
| *let-7* induction | | | |
| | HMGA2 | 0.29 | 6.00E-17 |
| | DICER1 | 0.39 | 1.12E-08 |
| | ARID3B | 0.49 | 0.0048 |
| | HDHD1A | 0.48 | 0.0059 |
FIG. 8B
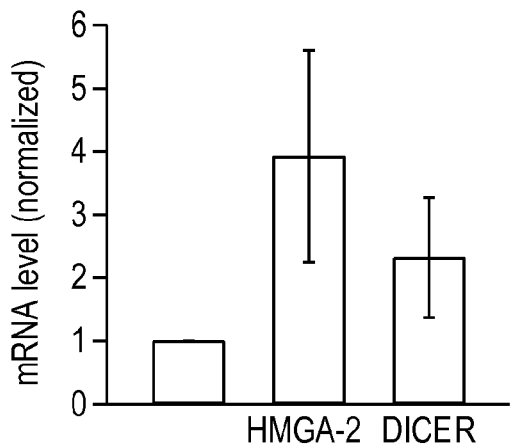
FIG. 8C
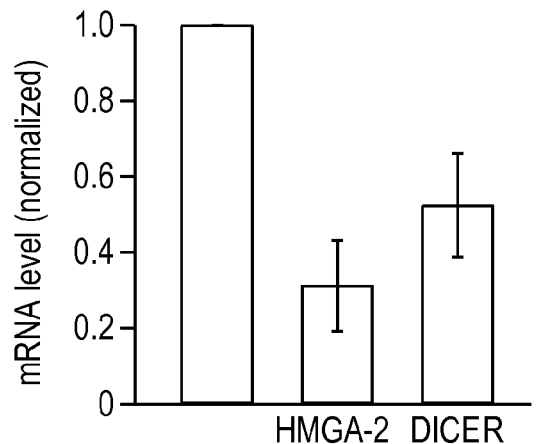

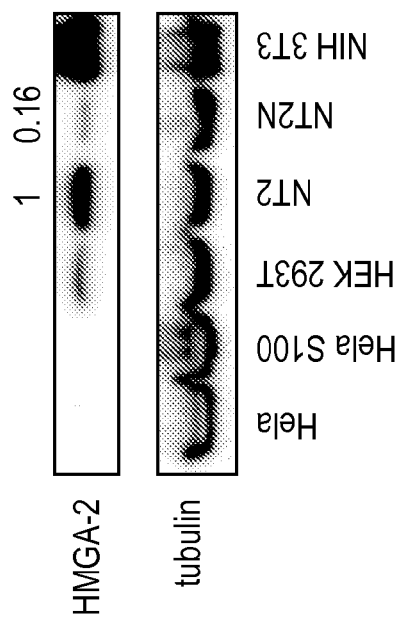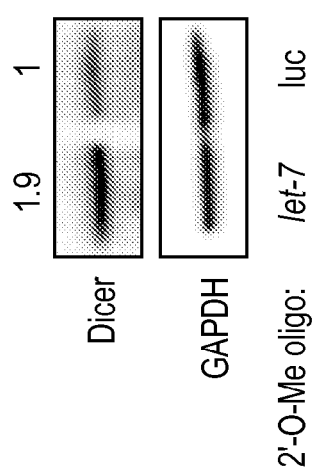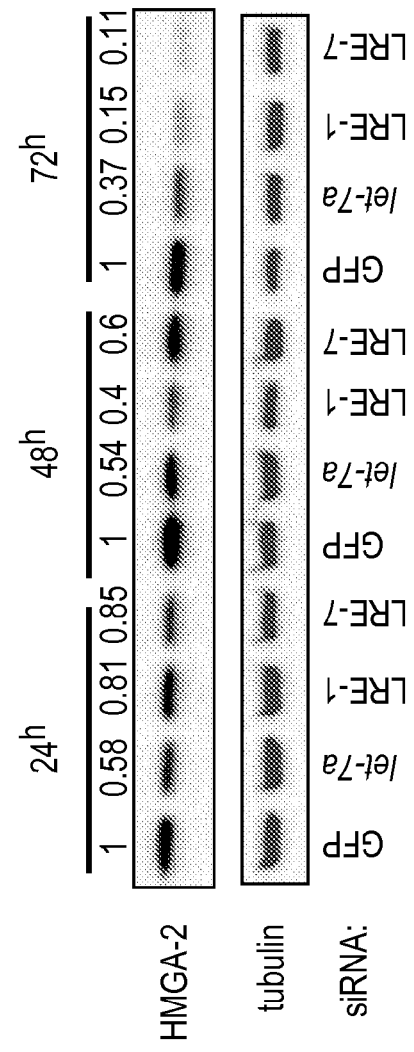
FIG. 9A
FIG. 9B
FIG. 9C

SEQUENCE-SPECIFIC INHIBITION OF SMALL RNA FUNCTION

RELATED APPLICATIONS

This application is a continuation of U.S. Ser. No. 10/998,364, entitled, "Sequence-Specific Inhibition of Small RNA Function," filed on Nov. 26, 2004, which claims the benefit of USSN 60/543,796, entitled "Sequence-Specific Inhibition of Small RNA Function," filed on Feb. 10, 2004, and USSN 60/525,474, entitled "Sequence-Specific Inhibition of Small RNA Function," filed on Nov. 26, 2003. The entire contents of these applications are hereby incorporated herein by reference.

STATEMENT AS TO FEDERALLY SPONSORED RESEARCH

Funding for the work described herein was at least in part provided by the federal government (N.I.H. grants GM62862-01 and GM65236-01, and GM58800).

BACKGROUND OF THE INVENTION

The endoribonuclease Dicer produces two types of small regulatory RNAs that regulate gene expression: small interfering RNAs (siRNAs) and microRNAs (miRNAs) (Bernstein et al., 2001; Grishok et al., 2001; Hutvágner et al., 2001; Ketting et al., 2001; Knight and Bass, 2001). In animals, siRNAs direct target mRNA cleavage (Elbashir et al., 2001c; Elbashir et al., 2001d), whereas miRNAs block target mRNA translation (Lee et al., 1993; Reinhart et al., 2000; Brennecke et al., 2003; Xu et al., 2003). Recent data suggest that both siRNAs and miRNAs incorporate into similar perhaps even identical protein complexes, and that a critical determinant of mRNA destruction versus translation regulation is the degree of sequence complementary between the small RNA and its mRNA target (Hutvágner and Zamore, 2002; Mourelatos et al., 2002; Zeng et al., 2002; Doench et al., 2003; Saxena et al., 2003; Zeng et al., 2003a).

Target RNA cleavage directed by siRNA is called RNA interference (RNAi). RNAi is a powerful method for the study of gene function in animals and plants and is being developed as a therapy for treating genetic disorders and viral infections. Biochemical studies in *Drosophila* S2 cells (Bernstein et al., 2001; Hammond et al., 2001a; Caudy et al., 2002; Liu et al., 2003) and affinity purification (Martinez et al., 2002) or immunoprecipitation (Hutvágner and Zamore, 2002) from cultured human HeLa cells have identified protein components of the RNAi effector complex, the RNA-induced silencing complex (RISC; the RISC complex also functions in miRNA-mediated translational silencing). Genetic mutations that disrupt RNAi in *C. elegans*, *Drosophila*, green algae, fungi and plants have likewise identified proteins required for RNAi (Cogoni and Macino, 1997; Cogoni and Macino, 1999a; Cogoni and Macino, 1999b; Ketting et al., 1999; Tabara et al., 1999; Catalanotto et al., 2000; Dalmay et al., 2000; Fagard et al., 2000; Grishok et al., 2000; Ketting and Plasterk, 2000; Mourrain et al., 2000; Wu-Scharf et al., 2000; Dalmay et al., 2001; Catalanotto et al., 2002; Grishok and Mello, 2002; Tabara et al., 2002; Tijsterman et al., 2002a; Tijsterman et al., 2002b). Key steps in the RNAi pathway have also emerged from studies of RNAi reconstituted in cell-free extracts (Tuschl et al., 1999; Zamore et al., 2000; Hammond et al., 2001b; Nykänen et al., 2001; Martinez et al., 2002; Schwarz et al., 2002; Tang et al., 2003).

Recently hundreds of miRNAs have been identified in animals and plants (Lagos-Quintana et al., 2001; Lau et al., 2001; Lee and Ambros, 2001; Lagos-Quintana et al., 2002; Reinhart et al., 2002; Ambros et al., 2003; Aravin et al., 2003; Brennecke and Cohen, 2003; Lim et al., 2003). Of these, the biological functions of at least four animal miRNAs are known. In *C. elegans*, the miRNAs lin-4 (Locus link ID 266860; Lee et al., 1993; Olsen and Ambros, 1999) and let-7 (Locus link ID 266954; Reinhart et al., 2000) regulate developmental timing, whereas the *Drosophila* miRNAs bantam (Locus link ID 117376) and miR-14 (Locus link ID 170868) control cell survival by repressing translation of pro-apoptotic genes (Brennecke et al., 2003; Xu et al., 2003). Computational approaches have also been described to assist in identifying the mRNA targets of other miRNAs (Enright et al., 2003; Lewis et al., 2003; Stark et al., 2003). Despite the widespread use of RNAi to 'knock down' gene function and the increasing body of evidence supporting a role for miRNAs in RNA silencing, the mechanisms by which these processes occur are not yet fully understood. Accordingly, there exists a need for a more complete understanding of the mechanisms underlying RNA silencing (e.g., RNAi, miRNA-mediated translational silencing), as well as for compounds which can regulate RNA silencing.

SUMMARY OF THE INVENTION

The present invention is based, at least in part, on the discovery that RISC inactivators are potent and irreversible inhibitors of small RNA-directed RNA silencing in vivo and in vitro. In particular, the invention is based, at least in part, on the discovery that 2'-O-methyl oligonucleotides are potent and irreversible inhibitors of small RNA-directed RNA silencing in vivo and in vitro. Accordingly, the present invention relates to methods of modulating (e.g., inhibiting) RNA silencing, in particular, microRNA (miRNA)-mediated and/or siRNA-mediated RNA silencing. The RNA silencing-inhibitory agents of the invention are suitable for use in modulating RNA silencing both in vitro and in vivo. In vivo methodologies are useful for both general RNA silencing modulatory purposes as well as in therapeutic applications in which RNA silencing modulation (e.g., inhibition) is desirable. Use of RNA silencing is of use in investigation of disease states, e.g., oncogenesis and infectious disease. Insulin secretion has recently been shown to be regulated by at least one miRNA (Poy et al. 2004), and a role for miRNAs has also been implicated in spinal muscular atrophy (SMA; Mourelatos et al. 2002). There is therefore mounting evidence that the activities of siRNAs and miRNAs could impact a broad range of disease states.

The present invention provides compositions for sequence-specific RISC inactivation and methods of use thereof. In particular, the invention provides RISC inactivators (e.g., 2'-O-methyl oligonucleotides, as well as similarly effective RISC inactivators, e.g., locked nucleic acid (LNA) and phosphorothioate-modified oligonucleotides) for modulating RNA silencing in a sequence-specific manner in vitro and in vivo. Methods for using RISC inactivators are also provided, including:

methods for identifying agents capable of modulating RNA silencing
methods for identifying RISC-associated factors.
methods for identifying and characterizing functions of miRNAs and siRNAs.
methods for monitoring inhibition of RNA silencing.
methods for measuring levels of programmed RISC.

Therapeutic methods and compositions incorporating RISC inactivators and therapeutic agents identified through use of RISC inactivators are also featured.

Other features and advantages of the invention will be apparent from the following detailed description and claims.

BRIEF DESCRIPTION OF THE DRAWINGS

FIG. 1A depicts sequences of the sense and anti-sense Pp-luc target RNAs (black), the siRNA (red, anti-sense strand; black, sense strand), and the sense and anti-sense 2'-O-methyl oligonucleotides (blue) used.

FIG. 4 shows that a 2'-O-methyl oligonucleotide was a potent inhibitor of RNAi in human cultured HeLa cells. In FIG. 4A-4D, HeLa cells were transfected with 1 nM (4A), 5 nM (4B), 10 nM (4C), or 25 nM (4D) siRNA targeting Pp-luc mRNA. The next day the cells were cotransfected with Rr-luc and Pp-luc expressing plasmids together with various amounts of a 31-nucleotide 2'-O-methyl oligonucleotide complementary to the anti-sense strand of the siRNA. The half-maximal concentration of 2'-O-methyl oligonucleotide required to inhibit (IC50) was determined by fitting the data to a sigmoidal curve using a Hill coefficient of one. FIG. 4E depicts IC50 plotted as a function of the concentration of transfected siRNA.

FIG. 7 depicts that let-7 is developmentally regulated in NT2 cells.

FIG. 8 shows that let-7 altered the RNA levels of its target genes. FIG. 8A shows putative let-7 target genes, for which expression was significantly altered upon let-7 inhibition in HeLa cells and let-7 over-expression in NT2 cells. FIG. 8B depicts results of real-time PCR analysis of HMGA2 and Dicer transcripts in HeLa cells upon inhibition of let-7 with a 2'-O-methyl oligonucleotide. FIG. 8C shows the results of real-time PCR analysis of HMGA2 and Dicer transcripts in NT2 cells upon transfection of let-7 siRNA.

FIG. 9 shows that expressed levels of HMGA2 and Dicer proteins were let-7 dependent. FIG. 9A demonstrates that Dicer expression was increased in HeLa cells upon let-7 inhibition, with relative Dicer protein levels indicated. FIG. 9B shows that HMGA2 protein expression was developmentally regulated in NT2 cells. Different human cell lines and mouse NIH3T3 cells were tested for HMGA2 expression, with relative levels of HMG2A expression indicated. HMGA2 expression was dramatically decreased in NT2N cells upon retinoic acid induced differentiation of NT2 cells. FIG. 9C depicts that let-7 repressed HMGA2 expression in NT2 cells. Cells were transfected with let-7 siRNA and two siRNAs that target the HMGA2 mRNA, with relative levels of HMGA2 protein indicated.

DETAILED DESCRIPTION OF THE INVENTION

Figure 1:
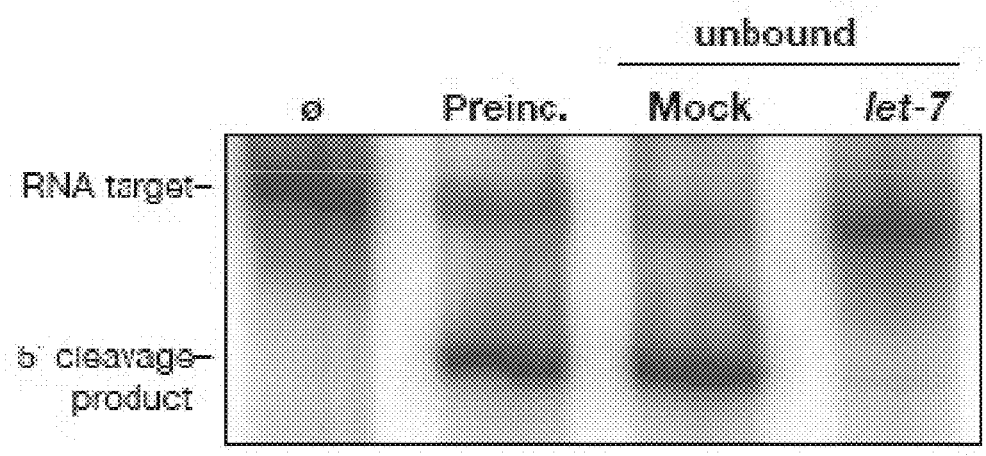
FIG. 1 shows that a 2'-O-methyl RNA oligonucleotide inhibited RNAi in vitro in *Drosophila* embryo lysate.

The present invention relates to the discovery of a method by which to selectively inhibit RNA silencing in a targeted, sequence-specific manner. The invention therefore features RISC inactivators (e.g., 2'-O-methyl oligonucleotides, and one of skill in the art will recognize that effective RISC inactivators may also be synthesized using oligonucleotides containing, e.g., locked nucleic acids (LNA), phosphorothioate modifications, or other equivalents). A form of RISC inactivator, specifically a 2'-O-methyl oligonucleotide, was identified as being capable of potently and irreversibly inhibiting small RNA-directed RNA silencing in vivo and in vitro. A 2'-O-methyl oligonucleotide complementary to an siRNA was shown to be capable of blocking mRNA cleavage in *Drosophila* embryo lysates and HeLa cell S100 extracts and in cultured human HeLa cells. In *Caenorhabditis elegans*, injection of the 2'-O-methyl oligonucleotide complementary to the miRNA let-7 induced a let-7 loss-of-function phenocopy. Using an immobilized 2'-O-methyl oligonucleotide, it was demonstrated that the *C. elegans* Argonaute proteins ALG-1 and ALG-2, which were previously implicated in let-7 function through genetic studies, were constituents of a let-7-containing protein-RNA complex. Thus, it was shown that 2'-O-methyl RNA oligonucleotides provide an efficient and straightforward way to block small RNA function in vivo and furthermore are useful for identifying small RNA-associated proteins that mediate RNA silencing pathways.

These experiments using 2'-O-methyl oligonucleotides also demonstrated that the acquisition of a target RNA by an siRNA-programmed RISC was far more efficient than the binding of an anti-sense oligonucleotide to the same region of the target. To demonstrate the utility of 2'-O-methyl oligonucleotides in probing RNA silencing pathways, it was shown that 2'-O-methyl oligonucleotides efficiently blocked siRNA-directed RISC activity in cell extracts and in cultured human HeLa cells. When injected into *Caenorhabditis elegans* larvae, a let-7-complementary 2'-O-methyl oligonucleotide could efficiently suppress lin-41 translational repression by the let-7 miRNA. Finally, a tethered 2'-O-methyl oligonucleotide was used to demonstrate association of the *C. elegans* Argonaute proteins ALG-1 and ALG-2 with let-7.

The methods of the present invention enable the extensive characterization of naturally-occurring microRNAs (miRNAs) and siRNAs. Hundreds of microRNAs (miRNAs) and endogenous small interfering RNAs (siRNAs) have been identified from both plants and animals, yet with few exceptions, little is known about their biochemical modes of action and even about their biological functions. The discovery of the invention that RISC-inactivating agents, specifically 2'-O-methyl oligonucleotides, effectively inhibit RNA silencing (e.g., RNAi, miRNA-mediated translational silencing) in a sequence-specific manner directly facilitates extensive characterization of both miRNAs and siRNAs. In addition, the methods of the present invention also enable methods for identifying therapeutic compounds capable of modulating RNA silencing activity.

RISC inactivators of the invention are of any size and/or chemical composition sufficient to inhibit RNA silencing, in particular, microRNA (miRNA)-mediated and/or siRNA-mediated RNA silencing. In exemplary embodiments, the RISC inactivators are oligonucleotides of between about 10-100 nucleotides (or modified nucleotides), preferably between about 10-40 nucleotides (or modified nucleotides) (e.g., ribonucleotides or modified ribonucleotides), for example, between about 15-35, e.g., about 15-20, 20-25, 25-30 or 30-35 (31, 32, 33, 34, 35) 40 nucleotides (or modified nucleotides) (e.g., ribonucleotides or modified ribonucleotides).

RNA silencing-inhibitory agents (RISC inactivators) are preferably sufficiently complementary to miRNA sequences or to siRNA sequences, in particular, the guide-strand or antisense strand sequences of an siRNA.

The invention further relates to methods for identifying miRNA-associating agents, for example, agents or compounds associated with miRNAs in vivo. In particular, the invention provides methods for isolating, identifying and/or characterizing constituents of miRNA-containing complexes, e.g., miRNA-containing protein-RNA complexes. Such constituents (e.g., miRNA-associated proteins) can be themselves used as modulators of RNA silencing pathways or can be used in further assays (e.g., screening assays) to identify compounds suitable for modulating such pathways.

In a preferred embodiment, the invention includes a method for inhibiting the RNA silencing of individual genes, through use of a RISC inactivator that is designed to anneal to the guide strand of an siRNA or miRNA, with said siRNA or miRNA normally functioning to direct RNA silencing of a specific target gene. In one embodiment, a cell containing an siRNA or miRNA that directs RNA silencing of a gene is contacted by a RISC inactivator sufficiently complementary to the guide strand of the siRNA or miRNA to achieve inhibition of the RNA silencing activity of the specific siRNA or miRNA to which the RISC inactivator is targeted. In a related embodiment, an organism is contacted by a RISC inactivator to achieve such gene-specific inhibition of RNA silencing.

In another embodiment, the RISC inactivators (RISC inhibitors) of the invention are utilized to identify factors that associate with siRNA or miRNA molecules. Specifically, a cell containing an siRNA or miRNA that directs RNA silencing of a specific gene is contacted with a RISC inactivator sufficiently complementary to the siRNA or miRNA to induce inhibition of the RNA silencing of a target gene normally directed by the siRNA or miRNA. Because the RISC inactivator anneals in a stable and specific manner to the siRNA or miRNA in the presence of RISC and associated factors, enrichment for the RISC inactivator or targeted siRNA or miRNA also enriches for RISC and other associated factors, thus allowing for identification of siRNA- or miRNA-associated factors.

In an additional embodiment, the RISC inactivator (RISC inhibitor) of the invention is nuclease-resistant.

In a further embodiment, the RISC inactivator (RISC inhibitor) of the invention is ribonuclease-resistant.

In a related embodiment, the RISC inactivator (RISC inhibitor) of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator (RISC inhibitor) of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In an additional embodiment, the cell or organism of the invention is a *Drosophila melanogaster* cell or organism; and a further embodiment specifies the *Drosophila melanogaster* cell or organism to be a *Drosophila melanogaster* embryo.

In another embodiment, the cell or organism of the invention is a *Caenorhabditis elegans* cell or organism.

In a further embodiment, the cell or organism of the invention is a mammalian cell or organism.

In another embodiment, the RISC inactivators of the invention are utilized to identify factors within a composition that associate with miRNA molecules. Specifically, a composition containing a miRNA that directs RNA silencing of a specific gene is contacted with a RISC inactivator sufficiently complementary to the miRNA to induce inhibition of the RNA silencing of a target gene normally directed by the miRNA. Because the RISC inactivator anneals in a stable and specific manner to the miRNA in the presence of RISC and associated factors, enrichment for the RISC inactivator or targeted miRNA also enriches for RISC and other associated factors, thus allowing for identification of miRNA-associated factors.

In a related embodiment, factors within a composition that associate with siRNA molecules are identified by the invention in the same manner as the method used to identify siRNA-associated factors. Specifically, a composition containing an siRNA that directs RNA silencing of a specific gene is contacted with a RISC inactivator sufficiently complementary to the siRNA to induce inhibition of the RNA silencing of a target gene normally directed by the siRNA. Because the RISC inactivator anneals in a stable and specific manner to the siRNA in the presence of RISC and associated factors, enrichment for the RISC inactivator or targeted siRNA also enriches for RISC and other associated factors, thus allowing for identification of siRNA-associated factors.

In an additional embodiment, the RISC inactivator (RISC inhibitor) of the invention is nuclease-resistant.

In a further embodiment, the RISC inactivator (RISC inhibitor) of the invention is ribonuclease-resistant.

In a related embodiment, the RISC inactivator (RISC inhibitor) of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator (RISC inhibitor) of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In one embodiment of the invention, the composition is a cell extract.

In a related embodiment, the composition is a *Drosophila melanogaster* cell extract; and in another embodiment, the composition is specified to be a *Drosophila melanogaster* embryo cell extract.

In an additional embodiment, the composition of the invention is a *Caenorhabditis elegans* cell extract.

In another embodiment, the composition of the invention is a mammalian cell extract.

The invention also enables detection of factors that associate with the RISC inactivator of the invention. In one embodiment, a RISC inactivator sufficiently complementary to the guide strand of an siRNA or miRNA is attached to a surface and then contacted with a composition comprising the siRNA or miRNA, causing the RISC inactivator and siRNA or miRNA to form a complex also associated with other factors, such that factors associated with the RISC inactivator of the invention are detected.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In an additional embodiment of the invention, the RISC inactivator of the invention is attached to the surface of a bead.

In another embodiment, the RISC inactivator of the invention is tethered to the surface of a streptavidin-coated bead via a 5' biotin linkage.

In another embodiment, the surface of the invention is a paramagnetic bead surface.

In an additional embodiment, the surface of the invention is a column.

In another embodiment, the composition of the invention is a cell extract comprising an siRNA or miRNA.

The invention also provides a method for identifying the active miRNAs of a composition. Accordingly, in one embodiment, the invention involves the process of contacting, with a cell extract comprising miRNAs, a series or array comprising RISC inactivators sufficiently complementary to guide strands of potential miRNAs (wherein the series or array is relatively enriched for oligonucleotides sufficiently complementary to guide strands of potential miRNAs, as compared to random or extant arrays or series of oligonucleotide, genomic, EST or mRNA sequences); and then detecting the association of cell extract miRNAs with the RISC inactivators, such that active miRNAs are identified.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In one embodiment, the cell extract is a *Drosophila melanogaster* cell extract; and in a related embodiment, the cell extract is specified to be a *Drosophila melanogaster* embryo cell extract.

In an additional embodiment, the cell extract of the invention is a *Caenorhabditis elegans* cell extract.

In another embodiment, the cell extract of the invention is a mammalian cell extract.

In a further embodiment, the polynucleotides of the cell extract of the invention are fluorescently labeled.

In a related embodiment, the polynucleotides of the cell extract of the invention are radioactively labeled.

In an additional embodiment, the RNAs (e.g., uracil moieties of polyribonucleotides) of the cell extracts are fluorescently labeled.

In a related embodiment, the RNAs (e.g., uracil moieties of polyribonucleotides) of the cell extracts are radioactively labeled.

The invention also enables monitoring of the extent to which sequence-specific inhibition of RNA silencing occurs. In one embodiment, the invention includes the procedure of contacting a cell expressing a reporter RNA and containing an siRNA or miRNA sufficiently complementary to the reporter RNA, with a RISC inactivator that is sufficiently complementary to the guide strand of the siRNA or miRNA, and then detecting the cleavage state of the reporter RNA, with the cleavage state of the reporter RNA thus indicating the level of sequence-specific inhibition of RNA silencing.

In a related embodiment, monitoring of the extent to which sequence-specific inhibition of RNA silencing occurs is achieved by contacting a cell extract containing a reporter RNA and an siRNA or miRNA sufficiently complementary to the reporter RNA, with a RISC inactivator that is sufficiently complementary to the guide strand of the siRNA or miRNA, and then detecting the cleavage state of the reporter RNA.

In another embodiment, monitoring of the extent to which sequence-specific inhibition of RNA silencing occurs is achieved by contacting an organism expressing a reporter RNA and containing an siRNA or miRNA sufficiently complementary to the reporter RNA, with a RISC inactivator that is sufficiently complementary to the guide strand of the siRNA or miRNA, and then detecting the cleavage state of the reporter RNA.

In an additional embodiment, monitoring of the extent to which sequence-specific inhibition of RNA silencing occurs is achieved by contacting a cell expressing a reporter RNA and containing an siRNA or miRNA sufficiently complementary to the reporter RNA, with a RISC inactivator that is sufficiently complementary to the guide strand of the siRNA or miRNA, and then detecting the level or activity of the polypeptide encoded by the reporter RNA.

In a related embodiment, monitoring of the extent to which sequence-specific inhibition of RNA silencing occurs is achieved by contacting a cell extract containing a reporter RNA and an siRNA or miRNA sufficiently complementary to the reporter RNA, with a RISC inactivator that is sufficiently complementary to the guide strand of the siRNA or miRNA, and then detecting the level or activity of the polypeptide encoded by the reporter RNA.

In a further embodiment, monitoring of the extent to which sequence-specific inhibition of RNA silencing occurs is achieved by contacting an organism expressing a reporter RNA and containing an siRNA or miRNA sufficiently complementary to the reporter RNA, with a RISC inactivator that is sufficiently complementary to the guide strand of the siRNA or miRNA, and then detecting the level or activity of the polypeptide encoded by the reporter RNA.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In an additional embodiment, the cell, cell extract or organism of the invention is a *Drosophila melanogaster* cell, cell extract or organism.

In another embodiment, the cell, cell extract or organism of the invention is a *Caenorhabditis elegans* cell, cell extract or organism.

In a further embodiment, the cell, cell extract or organism of the invention is a mammalian cell, cell extract or organism.

In an additional embodiment, the reporter RNA of the invention is radioactively labeled.

In another embodiment, the reporter RNA of the invention is fluorescently labeled.

The invention also allows for the identification of compounds capable of modulating the interaction of a RISC inactivator with a miRNA or siRNA. Accordingly, in one embodiment of the invention, a composition containing: a reporter RNA, a miRNA or siRNA sufficiently complementary to the reporter RNA, and a RISC inactivator sufficiently complementary to the guide strand of the miRNA or siRNA, are contacted with a compound. The cleavage state of the reporter RNA or the expression level or activity of the polypeptide encoded by the reporter RNA then detected, allowing for a compound that modulates the interaction of the RISC inactivator with a miRNA or siRNA to be identified.

In a related embodiment of the invention, the procedure to identify compounds capable of modulating the interaction of a RISC inactivator with a miRNA or siRNA is performed by contacting a cell or cell extract containing: a reporter RNA, a miRNA or siRNA sufficiently complementary to the reporter RNA, and a RISC inactivator sufficiently complementary to the guide strand of the miRNA or siRNA, with a compound. The cleavage state of the reporter RNA or the expression level or activity of the polypeptide encoded by the reporter RNA then detected, allowing for a compound that modulates the interaction of the RISC inactivator with a miRNA or siRNA to be identified.

In an additional embodiment of the invention, the procedure to identify compounds capable of modulating the interaction of a RISC inactivator with a miRNA or siRNA is performed by contacting an organism containing: a reporter RNA, a miRNA or siRNA sufficiently complementary to the reporter RNA, and a RISC inactivator sufficiently complementary to the guide strand of the miRNA or siRNA, with a compound. The cleavage state of the reporter RNA or the expression level or activity of the polypeptide encoded by the reporter RNA then detected, allowing for a compound that modulates the interaction of the RISC inactivator with a miRNA or siRNA to be identified.

In one embodiment, the test compound of the invention is selected from the group consisting of a small molecule, a peptide, a polynucleotide, an antibody or biologically active portion thereof, a peptidomimetic, and a non-peptide oligomer.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In an additional embodiment, the cell, cell extract or organism of the invention is a *Drosophila melanogaster* cell, cell extract or organism.

In another embodiment, the cell, cell extract or organism of the invention is a *Caenorhabditis elegans* cell, cell extract or organism.

In a further embodiment, the cell, cell extract or organism of the invention is a mammalian cell, cell extract or organism.

In an additional embodiment, the reporter RNA of the invention is radioactively labeled.

In another embodiment, the reporter RNA of the invention is fluorescently labeled.

The invention also enables identification of compounds that modulate the interaction of a factor associated with a (miRNA-RISC inactivator) complex. Accordingly, in one embodiment of the invention, a composition comprising a miRNA and a RISC inactivator sufficiently complementary to the guide strand of the miRNA are contacted by a compound, and the RISC inactivator or miRNA and any associated factors are then enriched for, allowing identification of a compound that modulates the interaction of a factor associated with the (miRNA-RISC inactivator) complex.

In a related embodiment of the invention, identification of a compound that modulates the interaction of a factor associated with a (siRNA-RISC inactivator) complex is performed. A composition comprising a siRNA and a RISC inactivator sufficiently complementary to the guide strand of the siRNA are contacted by a compound, and the RISC inactivator or siRNA and any associated factors are then enriched for, allowing for identification of a compound that modulates the interaction of a factor associated with the (siRNA-RISC inactivator) complex.

In one embodiment, the test compound of the invention is selected from the group consisting of a small molecule, a peptide, a polynucleotide, an antibody or biologically active portion thereof, a peptidomimetic, and a non-peptide oligomer.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In a further embodiment, the levels or identities of factors associated with the (miRNA-RISC inactivator) or (siRNA-RISC inactivator) complex are compared to an appropriate control.

In another embodiment, the levels or identities of factors associated with the (miRNA-RISC inactivator) or (siRNA-RISC inactivator) complex are compared to levels or identities of factors associated with the (miRNA-RISC inactivator) or (siRNA-RISC inactivator) complex in the absence of compound.

The invention additionally allows for measurement of the level of a programmed RISC for a gene. Accordingly, in one embodiment, a RISC inactivator sufficiently complementary to the guide strand of a siRNA or miRNA is attached to a surface and contacted with a composition comprising a labeled siRNA or miRNA, such that the level of programmed RISC for a gene is detected.

In a further embodiment, the siRNA or miRNA of the invention is radioactively labeled.

In an additional embodiment, the siRNA or miRNA of the invention is fluorescently labeled.

In an additional embodiment, the RISC inactivator of the invention is nuclease-resistant.

In a further embodiment, the RISC inactivator of the invention is ribonuclease-resistant.

In a related embodiment, the RISC inactivator of the invention is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In another embodiment, the RISC inactivator of the invention is modified with a moiety selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In another embodiment, the surface of the invention is a bead.

In a further embodiment, the RISC inactivator of the invention is tethered to a streptavidin bead via a 5' biotin linkage.

In one embodiment, the surface of the invention is a paramagnetic bead.

In another embodiment, the surface of the invention is a column.

In an additional embodiment, the composition of the invention is a cell extract comprising a siRNA or miRNA.

In a preferred embodiment, the invention is a composition comprising a RISC inactivator.

In a related embodiment, the RISC inactivator of the composition is nuclease-resistant.

In another embodiment, the RISC inactivator of the composition is ribonuclease-resistant.

In an additional embodiment, the RISC inactivator of the composition is a 2'-O-methyl oligonucleotide.

In a further embodiment, the RISC inactivator of the invention comprises an oligonucleotide containing at least one locked nucleic acid (LNA).

In an additional embodiment, the RISC inactivator of the invention comprises an oligonucleotide containing at least one phosphorothioate modification.

In a related embodiment, modification of the RISC inactivator is selected from the group consisting of the 2'-OH group replaced by a H, alkoxy or OR, halogen, SH, SR, amino (such as NH2, NHR, NR2,), or CN group, wherein R is lower alkyl, alkenyl, alkynyl, or aryl.

In another embodiment, the compositon comprising a RISC inactivator also comprises a pharmaceutically acceptable carrier.

The invention also enables development of pharmaceutical compositions. Accordingly, one embodiment of the invention consists of pharmaceutical composition comprising a RISC inactivator sufficiently complementary to the guide strand of an siRNA or miRNA.

In one embodiment of the invention, the RISC inactivator is between about 10-100 nucleotides (or modified nucleotides; e.g., ribonucleotides or modified ribonucleotides).

In a further embodiment of the invention, the RISC inactivator is between about 10-40 nucleotides (or modified nucleotides; e.g., ribonucleotides or modified ribonucleotides).

In an additional embodiment of the invention, the RISC inactivator is between about 15-35 nucleotides (or modified nucleotides; e.g., ribonucleotides or modified ribonucleotides).

In another embodiment of the invention, the RISC inactivator is between about 15-20 nucleotides (or modified nucleotides; e.g., ribonucleotides or modified ribonucleotides).

In an alternative embodiment of the invention, the RISC inactivator is between about 20-25 nucleotides (or modified nucleotides; e.g., ribonucleotides or modified ribonucleotides).

In a further embodiment of the invention, the RISC inactivator is between about 25-30 nucleotides (or modified nucleotides; e.g., ribonucleotides or modified ribonucleotides).

In another embodiment, the RISC inactivator of the invention is between about 30-35 (31, 32, 33, 34, 35) nucleotides (or modified nucleotides; e.g., ribonucleotides or modified ribonucleotides).

In a further embodiment, the RISC inactivator of the invention is between about 35-40 nucleotides (or modified nucleotides; e.g., ribonucleotides or modified ribonucleotides).

In another embodiment, the RISC inactivator is administered at about low nanomolar (e.g., about 0.1-20 nM) doses.

Another embodiment of the invention includes a pharmaceutical composition comprising a compound identified by the methods of the invention related to compound identification.

In an additional embodiment, a method for treating an RNA interference disease or disorder comprising administering any of the pharmaceutical compositions identified by the invention is addressed.

In a related embodiment, administration of the pharmaceutical composition of the invention treats cancer.

In another embodiment, administration of the pharmaceutical composition of the invention treats spinal muscular atrophy (SMA).

In a further embodiment, administration of the pharmaceutical composition of the invention treats diabetes.

An additional aspect of the invention features a method for inhibiting HMGA2 expression comprising contacting a cell with a let-7 polynucleotide or fragment thereof, such that HMGA2 expression is inhibited. A related aspect of the invention features a method for enhancing HMGA2 expression comprising contacting a cell that contains let-7 or a fragment thereof with a let-7-RISC inactivator (a RISC inactivator sufficiently complementary to the guide strand of let-7), such that HMGA2 expression is enhanced.

Another aspect of the invention features a method for inhibiting Dicer expression comprising contacting a cell with a let-7 polynucleotide or fragment thereof, such that Dicer expression is inhibited. A related aspect of the invention features a method for enhancing Dicer expression comprising contacting a cell that contains let-7 or a fragment thereof with a let-7-RISC inactivator (a RISC inactivator sufficiently complementary to the guide strand of let-7), such that Dicer expression is enhanced.

An additional aspect of the invention features a method for identifying a compound that modulates the interaction of let-7-RISC with a Dicer transcript, comprising contacting a cell containing let-7-RISC with a test compound and determining the expression level and/or activity of Dicer, such that a compound that modulates the interaction of let-7-RISC with Dicer transcript is identified.

Another aspect of the invention features a method for identifying RNAs modulated by an RNA silencing agent comprising contacting a cell that contains an RNA silencing agent with a RISC inactivator; comparing the RNA expression levels of the RISC inactivator-contacted cell with the RNA expression levels of a cell that is not contacted with the RISC inactivator; and identifying RNAs whose expression level is modulated by treatment with the RISC inactivator, such that RNAs modulated by the RNA silencing agent are identified.

A further aspect of the invention features a method for identifying polypeptides whose expression is modulated by an RNA silencing agent comprising contacting a cell that contains an RNA silencing agent with a RISC inactivator, then comparing the polypeptide expression levels of the RISC inactivator-contacted cell with the polypeptide expression levels of a cell that is not contacted with the RISC inactivator, and identifying polypeptides whose expression level is modulated by treatment with the RISC inactivator, such that polypeptides whose expression is modulated by the RNA silencing agent are identified.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH$_2$, NHR, NR$_2$, COOR, or OR, wherein R is substituted or unsubstituted C$_1$-C$_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs.

As used herein, the term "RISC inactivator" or "RISC inhibitor" refers to a nucleic acid-based agent which inactivates or inhibits RISC function in a sequence-specific manner. In particular, the agent inactivates or inhibits the siRNA or miRNA components of a RISC complex in a sequence-specific manner, i.e., the agent inactivates or inhibits a RISC complex containing a siRNA or miRNA having a sequence complementary (i.e., sufficiently complementary) to the sequence of the agent, but does not affect (i.e., appreciably affect) the function of RISC complexes containing guide RNAs (i.e., siRNA guide strands or miRNAs) unrelated in sequence. The RISC inactivators or RISC inhibitors of the invention are preferably resistant or refractory to RISC-directed endonucleolytic cleavage or translational control (i.e., the agents do not themselves act as RISC substrates, as would target mRNAs). Preferably the agent is modified to resist degradation (i.e., degradation by cellular nucleases, in particular, ribonucleases). Preferably, the RISC inactivators or RISC inhibitors of the invention act (or are effective) at a concentration (e.g., have an IC50) in the nanomolar range, for example, less than 500 nM, preferably less than 400 nM, more preferably less than 300, 250, 200, 150, 100, 75, 50, 25, 10, 5, 2 or 1 nM.

Preferred RISC inactivators (or RISC inhibitors) are modified oligonucleotides having a length of about 20 to 40 nucleotides (or nucleotide analogs), e.g., 20, 21, 22, 23, 24, 25, 26, 27, 28, 29, 30, 31, 32, 33, 34, 35, 36, 37, 38, 39, 40 nucleotides (or nucleotide analogs). In preferred embodiments, RISC inactivators (or RISC inhibitors) are modified oligonucleotides having a length of about 25 to 35 nucleotides (or nucleotide analogs). In other embodiments, RISC inactivators (or RISC inhibitors) are modified oligonucleotides having a length of about 5 to 60 nucleotides (or nucleotide analogs), or for example, about 5-10, 10-15, 15-20, 20-25, 25-30, 30-35, 35-40, 40-45, 45-50, 50-55, 55-60, 60 or more nucleotides (or nucleotide analogs).

The term "agent" and "compound" are used interchangeably herein.

As used herein, the term "nuclease-resistant oligonucleotide" refers to any oligonucleotide that has been modified to inhibit degradation by enzymes such as, for example, the exonucleases known to be present in the cytoplasm of a eukaryotic cell. RNA molecules (e.g., RNA oligonucleotides) are particularly at risk of degradation when combined with a composition comprising a cell extract or when introduced to a cell or organism, and a "ribonuclease-resistant" oligonucleotide is thus defined as a RISC inactivator that is relatively resistant to ribonuclease enzymes (e.g., exonucleases), as compared to an unmodified form of the same oligonucleotide. Preferred RISC inactivators of the invention include those that have been modified to render the oligonucleotide relatively nuclease-resistant or ribonuclease-resistant. In a preferred embodiment, the RISC inactivator of the invention has been modified with a 2'-O-methyl group.

The term "2'-O-methyl oligonucleotide", as used herein, possesses its art-recognized meaning.

The term "RNA interference" or "RNAi" (also referred to in the art as "gene silencing" and/or "target silencing", e.g., "target mRNA silencing"), as used herein, refers generally to a sequence-specific or selective process by which a target molecule (e.g., a target gene, protein or RNA) is downregulated. In specific embodiments, the process of "RNA interference" or "RNAi" features degradation or post-transcriptional silencing of RNA molecules, e.g., RNA molecules within a cell, said degradation or silencing being triggered by an RNAi agent. Degradation and post-transcriptional silencing of target RNA is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNA silencing agent", as used herein, refers to an RNA (or analog thereof), having sufficient sequence complementarity to a target RNA (i.e., the RNA being degraded) to direct RNA silencing (e.g., RNAi). An RNA silencing agent having a "sequence sufficiently complementary to a target RNA sequence to direct RNA silencing" means that the RNA silencing agent has a sequence sufficient to trigger the destruction or post-transcriptional silencing of the target RNA by the RNA silencing machinery (e.g., the RISC) or process. An RNA silencing agent having a "sequence sufficiently complementary to a target RNA sequence to direct RNA silencing" is also intended to mean that the RNA silencing agent has a sequence sufficient to trigger the translational inhibition of the target RNA by the RNA silencing machinery or process.

An RNA silencing agent having a "sequence sufficiently complementary to a target RNA encoded by the target DNA sequence such that the target DNA sequence is chromatically silenced" means that the RNA silencing agent has a sequence sufficient to induce transcriptional gene silencing, e.g., to down-modulate gene expression at or near the target DNA sequence, e.g., by inducing chromatin structural changes at or near the target DNA sequence.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, the term "microRNA" ("miRNA") refers to an RNA (or RNA analog) comprising the product of an endogenous, non-coding gene whose precursor RNA transcripts can form small stem-loops from which mature miRNAs are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003b; Lagos-Quintana et al., 2003; Lim et al., 2003a; Lim et al., 2003b). miRNAs are encoded in genes distinct from the mRNAs whose expression they control. Mature miRNAs represent the single stranded product of Dicer cleavage that then function as guide RNA fragments in mediating RNA silencing when incorporated into RISC.

As used herein, the term "antisense strand" of an siRNA or RNA silencing agent refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA silencing, (e.g., for RNAi, complementarity sufficient to trigger the destruction of the desired target mRNA by the RNAi machinery or process). The term "sense strand" or "second strand" of an siRNA or RNAi agent refers to a strand that is complementary to the antisense strand or first strand. Antisense and ssense strands can also be referred to as first or second strands, the first or second strand having complementarity to the target sequence and the respective second or first strand having complementarity to said first or second strand.

As used herein, the "5'end", as in the 5' end of an antisense strand, refers to the 5' terminal nucleotides, e.g., between one and about 5 nucleotides at the 5' terminus of the antisense strand. As used herein, the "3'end", as in the 3' end of a sense strand, refers to the region, e.g., a region of between one and about 5 nucleotides, that is complementary to the nucleotides of the 5' end of the complementary antisense strand.

As used herein, the term "guide strand" refers to a strand of an RNA silencing agent, e.g., an antisense strand of an siRNA duplex, that enters into RISC and directs cleavage or translational silencing of the target mRNA.

An siRNA or miRNA "that directs RNA silencing of a gene" is an siRNA or miRNA that has a sequence sufficiently complementary to the target mRNA encoded by a gene to trigger the post-transcriptional silencing or destruction of the target mRNA by the RNAi machinery or process.

An RISC inactivator having a "sequence sufficiently complementary to a RNA silencing agent, e.g., to a miRNA sequence or of a siRNA sequence" means that the RISC inactivator has a sequence sufficient to inhibit the activity of the RNA silencing agent, e.g., the miRNA or siRNA. RISC inactivators are preferably sufficiently complementary to miRNA sequences or to siRNA sequences, in particular, the guide-strand or antisense strand sequences of an siRNA.

The term "phosphorylated" means that at least one phosphate group is attached to a chemical (e.g., organic) compound. Phosphate groups can be attached, for example, to proteins or to sugar moieties via the following reaction: free hydroxyl group+phosphate donor→phosphate ester linkage. The term "5'phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). Mono-, di-, and triphosphates are common. Also intended to be included within the scope of the invention are phosphate group analogs which function in the same or similar manner as the mono-, di-, or triphosphate groups found in nature (see e.g., exemplified analogs.)

As used herein, the term "isolated RNA" (e.g., "isolated ssRNA", "isolated siRNA" or "isolated ss-siRNA") refers to RNA molecules which are substantially free of other cellular material, or culture medium when produced by recombinant techniques, or substantially free of chemical precursors or other chemicals when chemically synthesized.

A "target gene" is a gene whose expression is to be selectively inhibited or "silenced." This silencing is achieved by cleaving or translationally silencing the mRNA of the target gene (also referred to herein as the "target mRNA") by an siRNA or miRNA, e.g., an siRNA or miRNA that is created from an engineered RNA precursor by a cell's RNA silencing system. One portion or segment of a duplex stem of the RNA precursor is an anti-sense strand that is complementary, e.g., sufficiently complementary to trigger the destruction of the desired target mRNA by the RNAi machinery or process, to a section of about 18 to about 40 or more nucleotides of the mRNA of the target gene.

As used herein, the term "RISC" refers to the proteins and single-stranded polynucleotides that interact to recognize target RNA molecules. Demonstrated components of RISC include Dicer, R2D2 and the Argonaute family of proteins, as well as the guide strands of siRNAs and miRNAs. In the case of a RISC loaded with a single-stranded guide RNA derived from a siRNA, the RISC cleaves the target RNA molecule.

As used herein, the term "RNA silencing" refers to all forms of RISC-mediated small RNA-directed silencing and includes both RNAi (siRNA-mediated cleavage of target mRNA) and miRNA-mediated translational repression.

As used herein the term "compound" includes any reagent which is tested using the assays of the invention to determine whether it modulates RNAi activity. More than one compound, e.g., a plurality of compounds, can be tested at the same time for their ability to modulate RNAi activity in a screening assay.

In one embodiment, test compounds comprise any selection of the group consisting of a small molecule, a peptide, a polynucleotide, an antibody or biologically active portion thereof, a peptidomimetic, and a non-peptide oligomer.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A gene "involved" in a disorder includes a gene, the normal or aberrant expression or function of which effects or causes a disease or disorder or at least one symptom of said disease or disorder Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi-modulatory agent (e.g., an oligonucleotide, compound, etc., that alters sequence-specific RNAi activity) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. RISC Inactivators and RNA Molecules, e.g., siRNAs and miRNAs

The present invention features RISC inactivators, e.g., RISC inhibitors suitable for use in modulating RNA silencing both in vitro and in vivo. In vivo methodologies are useful for both general RNA silencing modulatory purposes as well as in therapeutic application in which RNA silencing modulation (e.g., inhibition) is desirable.

RISC inactivators of the invention are of any size and/or chemical composition sufficient to inhibit RNA silencing, in particular, microRNA (miRNA)-mediated translational repression and/or siRNA-mediated RNAi. In exemplary embodiments, the RISC inactivators are oligonucleotides of between about 10-100 nucleotides (or modified nucleotides), preferably between about 10-40 nucleotides (or modified nucleotides) (e.g., ribonucleotides or modified ribonucleotides), for example, between about 15-35, e.g., about 15-20, 20-25, 25-30, 30-35 (31, 32, 33, 34, 35), or 35-40 nucleotides (or modified nucleotides) (e.g., ribonucleotides or modified ribonucleotides). RISC inactivators are preferably sufficiently-complementary to miRNA sequences or to siRNA sequences, in particular, the guide-strand or antisense strand sequences of an siRNA.

In exemplary embodiments of the invention, RISC inactivators comprise oligonucleotides that contain 2'-O-methyl modifications. Many other forms of oligonucleotide modification may be used to generate RISC inactivators, including, for example, locked nucleic acids (oligonucleotides comprising at least one 2'-C,4'-C-oxy-methylene-linked bicyclic ribonucleotide monomer) and phosphorothioate modifications, with one of skill in the art recognizing other modifications capable of rendering an oligonucleotide an effective RISC inactivator.

The present invention also features RNAi agents, for example "single-stranded small interfering RNA molecules" ("ss-siRNA molecules" or "ss-siRNA"), methods of making said RNAi agents, e.g., ss-siRNA molecules, and methods (e.g., research and/or therapeutic methods) for using said RNAi agents, e.g., ss-siRNA molecules. Preferably, the ss-siRNA molecule has a length from about 10-50 or more nucleotides. More preferably, the ss-siRNA molecule has a length from about 15-45 nucleotides. Even more preferably, the ss-siRNA molecule has a length from about 19-40 nucleotides. The ss-siRNA molecules of the invention further have a sequence that is "sufficiently complementary" to a target mRNA sequence to direct target-specific RNA interference (RNAi), as defined herein, i.e., the ss-siRNA has a sequence sufficient to trigger the destruction of the target mRNA by the RNAi machinery or process. The ss-siRNA molecule can be designed such that every residue is complementary to a residue in the target molecule. Alternatively, substitutions can be made within the molecule to increase stability and/or enhance processing activity of said molecule. Substitutions can be made within the strand or can be made to residues a the ends of the strand. The 5'-terminus is, most preferably, phosphorylated (i.e., comprises a phosphate, diphosphate, or triphosphate group). Contrary to previous findings, however, that the 3' end of an siRNA be a hydroxyl group in order to facilitate RNAi, the present inventors have demonstrated that there is no requirement for a 3' hydroxyl group when the active agent is a ss-siRNA molecule. Accordingly, the invention features, in particular, ss-siRNA molecules wherein the 3' end (i.e., C3 of the 3' sugar) lacks a hydroxyl group (i.e., ss-siRNA molecules lacking a 3' hydroxyl or C3 hydroxyl on the 3' sugar (e.g., ribose or deoxyribose).

The target RNA cleavage reaction guided by siRNAs (e.g., by ss-siRNAs) is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In addition, active miRNAs are characteristically not 100% complementary to their target mRNAs, an attribute proposed to explain their tendency to act through translational repression, rather than cleavage, of their target mRNAs.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology= # of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 70% sequence identity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the RNAi-inhibitory agent and the RNAi agent, e.g., siRNA or miRNA, is preferred. Alternatively, the RNAi agent may be defined functionally as a nucleotide sequence (or oligonucleotide sequence) a portion of which is capable of hybridizing with the RNAi agent (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E.F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Modifications

In a preferred aspect, the RNA molecules, e.g., siRNAs and miRNAs, and RISC inactivators of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the ss-siRNAs in tissue culture medium.

In an especially preferred embodiment of the present invention the RNA molecules, e.g., siRNAs and miRNAs, and/or RISC inactivators may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined. RNA silencing agents of the invention also may be modified with chemical moieties (e.g., cholesterol) that improve the in vivo pharmacological properties of the RNA silencing agents.

RNA molecules and RISC inactivators may be produced enzymatically or by partial/total organic synthesis, any modified nibonucleotide can be introduced by in vitro enzymatic or organic synthesis. In one embodiment, a RNA molecule, e.g., siRNA or miRNA, or RISC inactivator is prepared chemically. Methods of synthesizing RNA and DNA molecules are known in the art, in particular, the chemical synthesis methods as de scribed in Verma and Eckstein (1998) *Annul Rev. Biochem.* 67:99-134. In another embodiment, a RNA molecule is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., single-stranded RNAs, and RISC inactivators can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In one embodiment, the target mRNA of an RNA silencing agent, e.g., siRNA or miRNA, of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of an RNA silencing agent, e.g., siRNA or miRNA, of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the RNA silencing agent, e.g., siRNA or miRNA, of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting an RNA silencing agent which controls expression of such proteins, valuable information regarding the function of said RNA silencing agent and/or proteins and therapeutic benefits which may be obtained from said inhibition may be obtained.

In certain embodiments, inhibition of RNA silencing agents with RISC inactivators can be used to identify and/or monitor gene products that are regulated by and/or associate with the RNA silencing agent. In exemplary embodiments, RNA and/or protein expression levels of cells, tissues or organisms contacted with a RISC inactivator are compared with expression levels of cells, tissues or organisms that have not been contacted with the RISC inactivator. Such a comparison thereby identifies the direct impact of inhibiting the RNA silencing agent on those gene products whose expression levels are surveyed. Such comparisons can be used to discover additional components of the tested RNA silencing agent's signaling pathway. Comparisons of RISC inactivator-treated and untreated states can additionally include comparison of such states in cells, tissues or organisms that express and/or contain the RNA silencing agent with RNA silencing agent-treated and untreated states in cells, tissues or organisms that do not normally express or contain the RNA silencing agent. Performance of such comparisons can enhance the specificity and efficacy of such approaches to identify RNA silencing agent pathway components.

Expression levels of surveyed genes may be assessed by any of a wide variety of well known methods for detecting expression of a transcribed nucleic acid or protein. Non-limiting examples of such methods include nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

A mixture of transcribed polynucleotides obtained from the assayed cells, tissues or organisms also can be contacted with a substrate, having fixed thereto a polynucleotide complementary to or homologous with at least a portion (e.g. at least 7, 10, 15, 20, 25, 30, 40, 50, 100, 500, or more nucleotide residues) of an assayed RNA e.g., an array of complementary polynucleotides (probes). If polynucleotides complementary to or homologous with multiple assayed RNAs are differentially detectable on the substrate (e.g. detectable using different chromophores, fluorophores or other tags, or fixed to different selected positions), then the levels of expression of a plurality of RNAs can be assessed simultaneously using a single substrate (e.g. a "gene chip" array of polynucleotides fixed at selected positions). When a method of assessing RNA expression is used which involves hybridization of one nucleic acid with another, it is preferred that the hybridization be performed under stringent hybridization conditions.

Because such methods rely on detection of a difference in expression levels of one or more RNAs, it is preferable that the level of expression of the RNA is significantly greater than the minimum detection limit of the method used to assess expression in at least one of the assayed cell populations, tissues or organisms.

When a plurality of RNAs are assayed, the level of expression of each RNA in a test sample can be compared with a baseline level of expression of each of the plurality of RNAs in a non-treated sample of the same type, either in a single reaction mixture (i.e. using reagents, such as different fluorescent probes, for each RNA) or in individual reaction mixtures corresponding to one or more of the RNAs. In an exemplary embodiment, a significantly increased level of expression of at least one of the plurality of RNAs in a RISC inactivator-treated cell population, tissue or organism that contains an RNA silencing agent, relative to the corresponding levels in an untreated cell population, tissue or organism that contains an RNA silencing agent, is an indication that the assayed RNA and/or gene encoding the assayed RNA is repressed by the inactivated RNA silencing agent, either directly or indirectly. Similarly, a significantly decreased level of expression of at least one of the plurality of assayed RNAs in an RNA silencing agent-treated cell population, tissue or organism (that does not contain the RNA silencing agent prior to treatment), relative to the corresponding levels of the assayed RNAs in an untreated cell population, tissue or organism (that does not contain the RNA silencing agent), is an indication that the assayed RNA silencing agent represses the assayed RNA and/or gene encoding the assayed RNA (either directly or indirectly). In exemplary embodiments, the expression modulation observed for assayed RNAs in one cell type (e.g., a cell containing an RNA silencing agent either treated or not treated with a RISC inactivator) may also be compared with the expression modulation observed for the assayed RNAs in another cell type (e.g., a cell that does not normally contain an RNA silencing agent, which is either treated or not treated with the RNA silencing agent). Such an approach can be used to identify RNA silencing agent-modulated RNAs/genes with even greater statistical confidence than approaches assessing treatment of a single type of cell with a single agent. Performance of parallel assays/expression profiles of cells (e.g., assays in duplicate, triplicate, etc.) can also enhance the statistical confidence of expression profile results. When a plurality of RNAs are assayed, 1, 2, 3, 4, 5, 8, 10, 12, 15, 20, 30, or 50 or more individual RNAs may be identified as modulated by the RNA silencing agent and/or RISC inactivator.

In one embodiment, RNA molecules, e.g., siRNAs or miRNAs, and/or RISC inactivators are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the ss-siRNA, miRNA or RISC inactivator. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses an RNA silencing agent, e.g., ss-siRNA, from a recombinant construct may be produced by introducing the construct into a zygote, an embryonic stem cell, or another multipotent cell derived from the appropriate organism.

II. Short Hairpin RNAs (shRNAs)

In certain featured embodiments, the invention provides shRNAs having efficacy in mediating RNA silencing. In contrast to short siRNA duplexes, short hairpin RNAs (shRNAs) mimic the natural precursors of miRNAs and enter at the top of the RNA silencing pathway. For this reason, shRNAs are believed to mediate RNA silencing more efficiently by being fed through the entire natural RNA silencing pathway.

Short Hairpin RNAs That Generate siRNAs shRNAs have a single strand that forms a duplex stem including two portions that are generally complementary, and a loop, that connects the two portions of the stem. In a preferred embodiment, short hairpin RNAs of the invention are artificial constructs engineered to deliver desired siRNAs.

In shRNAs of the invention, one portion of the duplex stem is a nucleic acid sequence that is complementary (or antisense) to the target mRNA. Thus, shRNAs include a duplex stem with two portions and a loop connecting the two stem portions. The two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs can be 2, 3, 4, 5, 6, 7, 8, 9, or more, e.g., 15 or 20, or more nucleotides in length.

shRNAs of the invention include the sequences of the desired siRNA duplex. The desired siRNA duplex, and thus both of the two stem portions in the shRNA, are selected by methods known in the art.

A defining feature of the shRNAs of the invention is that as a consequence of their length, sequence, and/or structure, they do not induce sequence non-specific responses, such as induction of the interferon response or apoptosis, or that they induce a lower level of such sequence non-specific responses than long, double-stranded RNA (>150 bp) that has been used to induce RNA silencing. For example, the interferon response is triggered by dsRNA longer than 30 base pairs.

III. Transgenes Encoding RNA Silencing Agents

The RNA silencing agents (e.g., siRNAs, miRNAs, etc.) and RISC inactivators of the invention can be synthesized by standard methods known in the art, e.g., by use of an automated nucleic acid synthesizer (such as are commercially available from Biosearch, Applied Biosystems, etc.). The RNA silencing agents and RISC inactivators can be used directly as described herein. The RNA silencing agents can be delivered to cells in vitro or in vivo in which it is desired to target a specific mRNA for destruction.

Moreover, certain RNA silencing agents (e.g., siRNAs) can be expressed from appropriate vectors by methods known in the field. A number of methods have been developed for delivering nucleic acid-based molecules to cells. For example, for in vivo delivery, molecules can be injected directly into a tissue site or administered systemically. In vitro delivery includes methods known in the art such as electroporation and lipofection.

To achieve intracellular concentrations of the nucleic acid molecule sufficient to suppress expression of endogenous mRNAs, one can use, for example, a recombinant DNA construct in which the oligonucleotide is placed under the control of a strong Pol III (e.g., U6 or Pol III H1-RNA promoter) or Pol II promoter. The use of such a construct to transfect target cells in vitro or in vivo will result in the transcription of sufficient amounts of the shRNA to lead to the production of an siRNA that can target a corresponding mRNA sequence for cleavage by RNAi to decrease the expression of the gene encoding that mRNA. (Or alternatively, such a construct may be made to express a miRNA.) For example, a vector can be introduced in vivo such that it is taken up by a cell and directs the transcription of shRNA or miRNA. Such a vector can remain episomal or become chromosomally integrated, as long as it can be transcribed to produce the desired shRNA or miRNA.

Such vectors can be constructed by recombinant DNA technology methods known in the art. Vectors can be plasmid, viral, or other vectors known in the art such as those described herein, used for replication and expression in mammalian cells or other targeted cell types. The nucleic acid sequences encoding the shRNAs or miRNAs of the invention can be prepared using known techniques. For example, two synthetic DNA oligonucleotides can be synthesized to create a novel gene encoding the entire shRNA or miRNA. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the shRNA or miRNA sequences (e.g., a cleavage and polyadenylation signal sequence from SV40 or a Pol III terminator sequence).

The invention also encompasses genetically engineered host cells that contain any of the foregoing expression vectors and thereby express the nucleic acid molecules of the invention in the host cell. The host cells can be cultured using known techniques and methods (see, e.g., Culture of Animal Cells (R. I. Freshney, Alan R. Liss, Inc. 1987); Molecular Cloning, Sambrook et al. (Cold Spring Harbor Laboratory Press, 1989)).

Successful introduction of the vectors of the invention into host cells can be monitored using various known methods. For example, transient transfection can be signaled with a reporter, such as a fluorescent marker, such as Green Fluorescent Protein (GFP). Stable transfection can be indicated using markers that provide the transfected cell with resistance to specific environmental factors (e.g., antibiotics and drugs), such as hygromycin B resistance, e.g., in insect cells and in mammalian cells.

IV. Methods of Introducing RNAs, RNA Silencing Agents, Vectors, and Host Cells

Physical methods of introducing nucleic acids include injection of a solution containing the nucleic acid (e.g., RNA molecule and/or RNA silencing agent), bombardment by particles covered by the nucleic acid (e.g., RNA molecule and/or RNA silencing agent), soaking the cell or organism in a solution of the nucleic acid (e.g., RNA molecule and/or RNA silencing agent), or electroporation of cell membranes in the presence of the nucleic acid (e.g., RNA molecule and/or RNA silencing agent). A viral construct packaged into a viral particle would accomplish both efficient introduction of an expression construct into the cell and transcription of a RNA molecule or silencing agent encoded by an expression construct. Other methods known in the art for introducing nucleic acids or nucleic acid-based agents to cells may be used, such as lipid-mediated carrier transport, chemical-mediated transport, such as calcium phosphate, and the like. Thus the nucleic acid-based agent may be introduced along with components that perform one or more of the following activities: enhance uptake by the cell, inhibit annealing of single strands, stabilize the single strands, or other-wise increase inhibition of the target gene.

The nucleic acid-based agent may be directly introduced into the cell (i.e., intracellularly); or introduced extracellularly into a cavity, interstitial space, into the circulation of an organism, introduced orally, or may be introduced by bathing a cell or organism in a solution containing the nucleic acid-based agent (e.g., RNA molecule and/or RNA silencing agent). Vascular or extravascular circulation, the blood or lymph system, and the cerebrospinal fluid are sites where the nucleic acid-based agent (e.g., RNA molecule and/or RNA silencing agent) may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include *Arabidopsis thaliana thaliana*; field crops (e.g., alfalfa, barley, bean, corn, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, fajoa, filbert, grape, grapefr-uit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber). Examples of vertebrate animals include fish, mammal, cattle, goat, pig, sheep, rodent, hamster, mouse, rat, primate, and human; invertebrate animals include nematodes, other worms, *drosophila*, and other insects.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of RNA silencing agent delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of a RNAi agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA silencing agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

The efficacy of RISC-inactivating agents of the invention can readily be assayed by detecting a decrease in or reversal of inhibition of gene expression, as described herein.

V. Arrays:

Expression arrays can be generated by attaching single-stranded nucleic acid molecules, e.g., polynucleotide probes, to a substrate in a two-dimensional matrix or array. Each single-stranded polynucleotide probe can comprise at least 5, 10, 15, 20, 25, 30, 35, 40, or 50 or more contiguous nucleotides. Arrays may contain probes for any number of RNAs, from a single RNA to a comprehensive collection of probes for the entire transcriptome (including, e.g., variant splice forms and variant sequences) of the cell, tissue or organism that is assayed.

A. Preparation of Arrays

Arrays are known in the art and consist of a surface to which probes that correspond in sequence to gene products (e.g., cDNAs, mRNAs, cRNAs, polypeptides, and fragments thereof), can be specifically hybridized or bound at a known position. The array can be a matrix in which each position represents a discrete binding site for a product encoded by a gene (e.g., a protein or RNA), and in which binding sites are present for products of most or almost all of the genes in the organism's genome. In one embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

B. Preparing Nucleic Acid Molecules for Arrays

As noted above, the "binding site" to which a particular cognate cDNA specifically hybridizes is usually a nucleic acid or nucleic acid analogue attached at that binding site. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e., fragments that do not share more than 10 bases of contiguous identical sequence with any other fragment on the array). Computer programs are useful in the design of primers with the required specificity and optimal amplification properties. See, e.g., Oligo version 5.0 (National Biosciences™). In the case of binding sites corresponding to very long genes, it will sometimes be desirable to amplify segments near the 3' end of the gene so that when oligo-dT primed cDNA probes are hybridized to the array, less-than-full length probes will bind efficiently. Typically each gene fragment on the array will be between about 50 bp and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc. San Diego, Calif., which is incorporated by reference in its entirety. It will be apparent that computer controlled robotic systems are useful for isolating and amplifying nucleic acids.

An alternative means for generating the nucleic acid molecules for the array is by synthesis of synthetic polynucleotides or oligonucleotides, e.g., using N-phosphonate or phosphoramidite chemistries (Froehler et al. (1986) *Nucleic Acid Res* 14:5399-5407; McBride et al. (1983) *Tetrahedron Lett.* 24:245-248). Synthetic sequences are between about 15 and about 500 bases in length, more typically between about 20 and about 50 bases. In some embodiments, synthetic nucleic acids include non-natural bases, e.g., inosine. As noted above, nucleic acid molecule analogues may be used as binding sites for hybridization. An example of a suitable nucleic acid analogue is peptide nucleic acid (see, e.g., Egholm et al. (1993) *Nature* 365:566-568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al. (1995) *Genomics* 29:207-209). In yet another embodiment, the polynucleotide of the binding sites is RNA.

C. Attaching Nucleic Acid Molecules to the Solid Surface

The nucleic acid molecule or analogue are attached to a solid support, which may be made from glass, plastic (e.g., polypropylene, nylon), polyacrylamide, nitrocellulose, or other materials. An example of a method for attaching the nucleic acid molecules to a surface is by printing on glass plates, as is described generally by Schena et al. (1995) *Science* 270:467-470, the contents of which are expressly incorporated herein by reference. This method is especially useful for preparing arrays of cDNA. See also DeRisi et al. (1996) *Nature Genetics* 14:457-460; Shalon et al. (1996) *Genome Res.* 6:639-645; and Schena et al. (1995) *Proc. Natl. Acad. Sci. USA* 93:10539-11286. Each of the aforementioned articles is incorporated by reference in its entirety.

A second example of a method for making arrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., (1991) *Science* 251:767-773; Pease et al., (1994) *Proc. Natl. Acad. Sci. USA* 91:5022-5026; Lockhart et al. (1996) *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al. (1996) Biosensors & Bioelectronics 11: 687-90). When these methods are used, oligonucleotides (e.g., 20-mers) of known sequence are synthesized directly on a surface such as a derivatized glass slide. In one embodiment, the array produced is redundant, with several oligonucleotide molecules per RNA. Oligonucleotide probes can be chosen to detect alternatively spliced mRNAs.

Other methods for making arrays, e.g., by masking (Maskos and Southern, 1992, Nuc. Acids Res. 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989, which is hereby incorporated in its entirety), could be used, although, as will be recognized by those of skill in the art, very small arrays will be preferred because hybridization volumes will be smaller.

Another method for making arrays is to directly deposit the probe on to the array surface. In such an embodiment probes will bind non-covalently or covalently to the array depending on the surface of the array and characteristics of the probe. In preferred embodiments the array has an epoxy coating on top of a glass microscope slide and the probe is modified at the amino terminal by an amine group. This combination of array surface and probe modification results in the covalent binding of the probe. Other methods of coating the array surface include using acrylamide, sialinization and nitrocellulose. There are several methods for direct deposit of the probes on to the array surface. In one embodiment, the probes are deposited using a pin dispense technique. In this technique, pins deposit probes onto the surface either using contact or non-contact printing. One preferred embodiment is non-contact printing using quill tip pins. Another embodiment uses piezo electric dispensing to deposit the probes.

Control composition may be present on the array including compositions comprising oligonucleotides or polynucleotides corresponding to genomic DNA, housekeeping genes, negative and positive control genes, and the like. These latter types of compositions are not "unique", i.e., they are "common." In other words, they are calibrating or control genes whose function is not to tell whether a particular "key" gene of interest is expressed, but rather to provide other useful information, such as background or basal level of expression. The percentage of samples which are made of unique oligonucleotides or polynucleotide that correspond to the same type of gene is generally at least about 30%, and usually at least about 60% and more usually at least about 80%.

D. Generating Labeled Probes

Methods for preparing total and poly(A)+ RNA are well known and are described generally in Sambrook et al., supra. In one embodiment, RNA is extracted from cells of the various types of interest in this invention using guanidinium thiocyanate lysis followed by CsCl centrifugation (Chirgwin et al. (1979) *Biochemistry* 18:5294-5299). Poly(A)+ RNA is selected by selection with oligo-dT cellulose (see Sambrook et al., supra).

Labeled cDNA is prepared from mRNA by oligo dT-primed or random-primed reverse transcription, both of which are well known in the art (see e.g., Klug and Berger, (1987) *Methods Enzymol.* 152:316-325). Reverse transcription may be carried out in the presence of a dNTP conjugated to a detectable label, e.g., a radioactive or fluorescently labeled dNTP. Alternatively, isolated mRNA can be converted to labeled antisense RNA synthesized by in vitro transcription of double-stranded cDNA in the presence of labeled dNTPs (Lockhart et al. (1996) *Nature Biotech.* 14:1675, the contents of which are expressly incorporated herein by reference). In alternative embodiments, the cDNA or RNA probe can be synthesized in the absence of detectable label and may be labeled subsequently, e.g., by incorporating biotinylated dNTPs or rNTP, or some similar means (e.g., photo-crosslinking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus™), Cy2, Cy3, Cy3.5, Cy5, Cy5.5, Cy7, Fluor X (Amersham™) and others (see, e.g., Kricka (1992) *Nonisotopic DNA Probe Techniques*, Academic Press San Diego, Calif.). It will be appreciated that pairs of fluorophores are chosen that have distinct emission spectra so that they can be easily distinguished.

A label other than a fluorescent label may also be used. For example, a radioactive label, or a pair of radioactive labels with distinct emission spectra, can be used (see Zhao et al. (1995) *Gene* 156:207; Pietu et al. (1996) *Genome Res.* 6:492).

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham™)) with reverse transcriptase (e.g., SuperScript™ II, LTI Inc.) at 42° C. for 60 min.

E. Generation of Targets

In one detection method, the array of immobilized nucleic acid molecules, or probes, is contacted with a target sample containing target nucleic acid molecules, to which a radioactive or flourescent label is attached. Target nucleic acid molecules hybridize to the probes on the array and any non-hybridized nucleic acid molecules are removed. For fluorescently labeled targets, the array containing the hybridized target nucleic acid molecules are exposed to light which excites the flourescent label. The resulting fluorescent intensity, or brightness, is detected. Alternatively, for radioactively labeled targets, the emissions of the radioactive label are detected.

In one embodiment, the target cDNA is generated from RNA derived from selected cell, tissue or organism samples (target samples). The cDNA may be labeled with a molecule which specifically binds with a second molecule which is labeled with one of the detection labels mentioned above for the detection of hybridization. In one embodiment, the cDNA is synthesized using a biotinylated dNTP. The biotinylated target cDNA is then hybridized to the array. There is then a second hybridization using streptavidin labeled with an appropriate fluorphore. The streptavidin will bind specifically to the biotinylated cDNA resulting in the detection of cDNA hybridization to the probe. In another embodiment, the cDNA is synthesized using specific primer sequences which add a capture sequence as the cDNA is being synthesized. The cDNA with the capture sequence is hybridized to the probes on the array. A second hybridization is performed using a fluorescently labeled molecule which binds specifically to the capture sequence, resulting in the detection of cDNA hybridization to the probe. Detection can be visual or with computer assistance.

F. Hybridization to Arrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acid molecules are described in Sambrook et al., supra, and in Ausubel et al., 1987, *Current Protocols in Molecular Biology*, Greene Publishing and Wiley-Interscience, New York, which is incorporated in its entirety for all purposes. Such stringent conditions are known to those skilled in the art and can be found in sections 6.3.1-6.3.6 of Current Protocols in Molecular Biology, John Wiley & Sons, N.Y. (1989). A non-limiting example of stringent hybridization conditions are hybridization in 6× sodium chloride/sodium citrate (SSC) at about 45° C., followed by one or more washes in 0.2×SSC, 0.1% SDS at 50-65° C. Useful hybridization conditions are also provided in, e.g., Tijessen, 1993, *Hybridization With Nucleic Acid Probes*, Elsevier Science Publishers B. V. and Kricka, 1992, *Nonisotopic DNA Probe Techniques*, Academic Press San Diego, Calif.

G. Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA array system for analyzing complex DNA samples using two-color fluorescent probe hybridization, Genome Research 6:639-645, which is incorporated by reference in its entirety for all purposes). The arrays may be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices 35 are described in Schena et al., 1996, Genome Res. 6:639-645 and in other references cited herein. Alternatively, the fiber-optic bundle described by Ferguson et al., 1996, Nature Biotech. 14:1681-1684, may be used to monitor mRNA abundance levels at a large number of sites simultaneously.

Signals are recorded and, in one embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event. According to the method of the invention, the relative abundance of an mRNA in two cells or cell lines is scored as a perturbation (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of differences of an order of about 2-fold and above, but more sensitive methods are expected to be developed.

In many cases, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In another embodiment, a single fluorophore is used and all of the hybridizations from the samples are detected at a single wave length. In this method, the samples are all compared with each other to determine expression levels. The expression levels for the membrane associated molecules are determined by comparing fluorescence intensity values from all of the samples from the same wavelength. There are several different methods used for data analysis using a single fluorphore for hybridization. One method is using global normalization. Briefly, the intensity values from all of the sequences are averaged for each sample. All of the sample intensity averages are then averaged to determine the experimental intensity average. A correction factor is calculated for each sample by dividing the experimental intensity average by the sample averages. All of the sequence intensity values are multiplied by the correction factor. Following normalization, the treated sample values are divided by the untreated sample values to determine the fold expression change.

Another method to analyze the intensity values uses a nonparametric analysis. Nonparametric statistical analysis of microarray data is performed by Spearman Rank Analysis. In the first method, each gene is ranked in order of measured fluorescence/radiolabel intensity within each sample and ranks are compared between test samples and grouped control samples. The statistical significance of each comparison is recorded. In the second method, each gene is ranked in order of measured fluorescence/radiolabel intensity across samples and ranks are compared between test samples and grouped control samples. The statistical significance of each comparison is recorded. For each method, each gene is counted for the number of test samples that had statistically higher rank than the control samples for each treatment.

VI. Methods of Treatment:

The present invention provides for both prophylactic and therapeutic methods of treating a subject at risk of (or susceptible to) a disorder or having a disorder associated with aberrant or unwanted gene expression or activity. "Treatment", or "treating" as used herein, is defined as the application or administration of a therapeutic agent (e.g., small RNA-inhibitory agent, e.g., siRNA-inhibitory agent) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., a RISC inactivator). Exemplary embodiments feature methods for specifically inactivating an RNAi agent (e.g., an siRNA) by administering a RISC inactivator of the present invention. Use of a RISC inactivator allows, for example, for temporal regulation of, e.g., siRNA treatment in a subject where such treatment is detrimental if performed for extended duration. RISC inactivators of the invention may also be used therapeutically to inhibit aberrant or unwanted miRNA activity. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., RISC inactivator) that is specific for the small RNA which targets a gene or protein (e.g., is specific for the small RNA, e.g., siRNA or miRNA, that targets an mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

3. Pharmacogenomics

The therapeutic agents (e.g., RISC inactivator) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose- 6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, a small RNA-inhibitory agent, e.g., siRNA-inhibitory agent as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

VI. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

VII. Screening Assays

A number of preferred methods of the invention relate to identifying and/or characterizing potential pharmacological agents, e.g., identifying new pharmacological agents from a collection of test substances and/or characterizing mechanisms of action and/or side effects of known pharmacological agents.

The invention provides methods (also referred to herein as "screening assays") for identifying modulators, i.e., candidate or test compounds or agents (e.g., peptides, peptidomimetics, peptoids, small molecules or other drugs) which (a) have a modulatory (e.g., stimulatory or inhibitory) effect on the activity of a RISC inactivator of the invention or, more specifically, (b) have a modulatory effect on the interactions of a RISC inactivator sufficiently complementary to an siRNA or miRNA with the siRNA or miRNA to which the siRNA or miRNA is complementary or (c) have a modulatory effect on the interactions of a RISC inactivator-siRNA or RISC inactivator-miRNA complex with associated factors (e.g., peptide, protein, hormone, co-factor, or nucleic acid, such as RISC components or RISC-associated factors), or (d) elicit a modulatory effect on RNA silencing by impacting the activity of a RISC inactivator of the invention. Such assays typically comprise a reaction between a RISC inactivator of the invention, an siRNA or miRNA to which the RISC inactivator is sufficiently complementary, and one or more assay components. The other components may be either the test compound itself, or any combination comprising test compound, reporter RNA, cells, cell extracts or organisms.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the library is a natural product library, e.g., a library produced by a bacterial, fungal, or yeast culture. In another preferred embodiment, the library is a synthetic compound library.

In one embodiment, the invention provides assays for screening for cellular factors which bind to RISC inactivator-miRNA- or RISC inactivator-siRNA-loaded RISC. Determining the ability of the cellular factor to directly bind to a protein can be accomplished, for example, by coupling the factor with a radioisotope, fluor or enzymatic label such that binding of the factor to the complex (e.g., RISC) can be determined by detecting the labeled marker factor in a complex. For example, factors (e.g., cellular polypeptides or polynucleotides) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product. Or fluorescent labeling of test factors may be performed to allow for fluorescence-based detection of factor binding.

In another embodiment, the invention provides assays for screening candidate or test compounds which modulate the association RISC inactivators of the invention with miRNAs or siRNAs, and thereby elicit an effect on RNA silencing. Screens for compounds that modulate RISC inactivator-miRNA, RISC inactivator-siRNA and/or RNA silencing activity can be performed in a number of ways. In one aspect of the invention, assessment of the effect of a potential RNA silencing modulatory agent, e.g., a test compound, on RISC inactivator-miRNA interaction, RISC inactivator-siRNA interaction or RNAi activity, may be examined by subjecting the compositions, cells, and cell extracts of the invention to the potential RISC inactivator-miRNA interaction, RISC inactivator-siRNA interaction or RNA silencing modulatory agent in a tube or related type of vessel. Screening of a library of compounds for the purpose of performing a high-throughput examination of the effect(s) of a large number of compounds on the RISC inactivator-miRNA interaction, RISC inactivator-siRNA interaction or RNA silencing activity of the invention's compositions, cells, organisms and lysates can also be performed, for example, in microwells. RISC inactivator-miRNA- and RISC inactivator-siRNA-containing compositions, cells, organisms, and lysates of the invention can also be screened against a matrix of test compounds to identify compounds capable of modulating the interaction of RISC inactivators of the invention with miRNAs or siRNAs.

Monitoring of RNA silencing in such screening assays can involve a number of assay readouts, e.g., the cleavage state of a target reporter RNA, expression or activity level of the polypeptide encoded by the target reporter RNA.

Detection of the interaction of the RISC inactivators of the invention with other polypeptides and nucleic acids can be performed, for example, through use of chemical crosslinking and immunoprecipitation methods, isolation of complexes through affinity column methodologies, or other art-recognized methods.

The skilled artisan will appreciate that the enumerated organisms are also useful for practicing other aspects of the invention, e.g., making transgenic organisms as described infra.

This invention is further illustrated by the following examples which should not be construed as limiting. The contents of all references, patents and published patent applications cited throughout this application are incorporated herein by reference.

EXAMPLES

The following materials, methods, and examples are illustrative only and not intended to be limiting.

Materials and Methods for Examples 1-5

General Methods

*Drosophila* embryo lysate preparation, in vitro RNAi reactions, and cap-labeling of target RNAs were as described (Haley et al., 2003). Target RNAs were used at ~3 nM concentration. Cleavage products of RNAi reactions were analyzed by electrophoresis on 5% or 8% denaturing acrylamide gels. Gels were dried, exposed to image plates, then scanned with a FLA-5000 phosphorimager (Fuji). Images were analyzed using Image Reader FLA-5000 version 1.0 (Fuji) and Image Gauge version 3.45 (Fuji). Data analysis was performed using Excel (Microsoft) and Igor Pro 5.0 (Wavemetrics).

siRNA and 2'-O-methyl oligonucleotides

Synthetic siRNA (Dharmacon) was deprotected according to the manufacturer, annealed (Elbashir et al., 2001c; Elbashir et al., 2001d), and used at 50 nM final concentration unless otherwise noted. 2'-O-methyl oligonucleotides (IDT or Dharmacon) were: 5'-CAU CAC GUA CGC GGA AUA CUU CGA AAU GUC C-3' (SEQ ID NO: 1) and 5'-Bio-CAU CAC GUA CGC GGA AUA CUU CGA AAU GUC C-3' (complementary to the Pp-luc siRNA sense strand; SEQ ID NO: 2) 5'-GGA CAU UUC GAA GUA UUC CGC GUA CGU GAU G-3' (SEQ ID NO: 3) and 5'-Bio-A CAU UUC GAA GUA UUC CGC GUA CGU GAU GUU-3' (complementary to the Pp-luc anti-sense strand; SEQ ID NO: 4); 5'-Bio-UCU UCA CUA UAC AAC CUA CUA CCU CAA CCU U-3' (complementary to let-7; SEQ ID NO: 5); 5' Biotin was attached via a six-carbon spacer arm.

Immobilized 2'-O-methyl Oligonucleotide Capture of RISC 10 pmol biotinylated 2'-O-methyl oligonucleotide was incubated for 1 hour on ice in lysis buffer containing 2 mM DTT with 50 µl Dynabeads M280 (as a suspension as provided by the manufacturer; Dynal) to immobilize the oligonucleotide on the beads. To ensure that the tethered oligonucleotide remained in excess when more than 50 nM siRNA was used, 20 pmol biotinylated 2'-O-methyl oligonucleotide was immobilized. For RISC capture assays, siRNA was pre-incubated in a standard 50 µl in vitro RNAi reaction for 15 minutes at 25° C. Then, the immobilized 2'-O-methyl oligonucleotide was added to the reaction and incubation continued for 1 hour at 25° C. After incubation, beads were collected using a magnetic stand (Dynal). The unbound supernatant was recovered and an aliquot assayed for RISC activity as previously described (Elbashir et al., 2001c; Nykänen et al., 2001) to confirm that RISC depletion was complete. The beads were then washed three times with ice-cold lysis buffer containing 0.1% (w/v) NP-40 and 2 mM DTT followed by a wash without NP-40. To determine the amount of RISC formed, input and bound radioactivity was determined by scintillation counting (Beckman). To isolate let-7-containing complexes from *C. elegans* adults, 20 pmol of immobilized 2'-O-methyl oligonucleotide was incubated with 1 mg total protein.

Sequential Transfection

HeLa S3 cells were transfected in a 24-well plate (200 mm per well) using Lipofectamine 2000 (GIBCO) according to the manufacturer's protocol first with various concentrations of siRNA targeting Pp-luc mRNA. After 6 hours the cells were washed with PBS and the media replaced. On the next day, the cells were cotransfected with *Renilla reniformis* (Accession Number AF025846) (0.1 µg/well) and *Photinus pyralis* (Accession Number X65324) luciferase-expressing plasmids (0.25 µg/well) and 2'-O-methyl oligonucleotides using Lipofectamine 2000 (GIBCO) according to the manufacturer protocol. Twenty-four hours later, the luciferase activity was measured with the Dual Luciferase assay kit (Promega) using a Mediators PhL luminometer.

Worm Injection

For in vivo inhibition of let-7 function, 1 mg/ml let-7-complementary 2'-O methyl oligonucleotide in water (100 µM) was injected into either wild-type (N2) or lin-41(ma104) L2 larvae. Injection of L2 larvae was essentially as described (Conte and Mello, 2003). The 2'-O-methyl oligonucleotide solution was injected into the body cavity of the larva using the low flow and pressure setting to prevent animals from dying. Despite these precautions, ~60% of the animals do not survive injection, irrespective of the oligonucleotide injected. let-7 phenotypes were also observed at 10 µM oligonucleotide, but were less penetrant. Phenotypes were scored after the injected animals survived to adulthood.

Expression Profiling of RISC Inactivator- and let-7-Treated and Untreated Cells

Experiments were performed in triplicate for each state (HeLa cells treated with let-7-RISC inactivator, untreated HeLa cells, NT2 cells treated with let-7, untreated NT2 cells). Total RNA extracted from samples was used to generate cRNA target, subsequently hybridized to human U133A oligonucleotide probe arrays (purchased from Affymetrix, Santa Clara, Calif.). cRNA preparation was performed using the Affymetrix GeneChip® one-cycle cDNA synthesis kit followed by labeling with the Affymetrix GeneChip® IVT labeling kit. Hybridization and data analysis was performed by the MIT microarray facility using standard methods (see, e.g., Ruan et al. *Diabetes* 51, 3176-3188; Bhattacharjee et al. *Proc. Natl. Acad. Sci. USA* 98, 13790-13795; Golub et al. *Science* 286, 531-537). All experimental expression profiles were normalized to the expression profile of cells treated separately with a non-specific 2'-O-methyl oligonucleotide and GFP siRNA.

Other Methods

Synchronized transgenic animals carrying GFP::ALG-1, GFP::ALG-2 were harvested at adulthood and homogenized in ice-cold buffer (25 mM HEPES-NaOH (pH 7.4), 150 mM NaCl, 1 mM EDTA, 1 mM DTT, 10% (v/v) glycerol, 0.5% (v/v) Triton X-100, 2% (v/v) SUPERaseIn (Ambion) and Mini Complete Protease Inhibitor cocktail (1 tablet/10 ml solution) (Roche)) using a stainless steel Dounce homogenizer (Wheaton). The homogenized extract was clarified by a centrifugation at 13,817×g for 10 minutes at 4° C.

To recover the proteins associated with the let-7 miRNA, the beads were boiled for 10 minutes in 20 µL SDS loading buffer (10 mM Tris-HCl (pH6.8), 2% (w/v) SDS, 100 mM DTT and 10% (v/v) glycerol). Proteins were resolved by SDS-PAGE on an 8% gel, and transferred to Hybond-C membrane (Amersham Biosciences). To detect GFP-tagged ALG-1, ALG-2, and RDE-4 proteins, the membrane was incubated overnight at 4° C. with either monoclonal anti-GFP (Roche) or an affinity purified polyclonal anti-RDE-4 antibody (Tabara et al, 2003) diluted 1:1000 into TBST-milk solution (100 mM Tris-HCl (pH 7.5), 150 mM NaCl, 0.1% (v/v) Tween-20 and 5% (w/v) dried milk), incubated 1 hr at room temperature with either anti-mouse (GFP-tagged ALG-1/ALG-2) or anti-rabbit (RDE-4) HRP-conjugated secondary antibody (Jackson Laboratories) diluted 1:5,000 in TBST, then visualized by enhanced chemuliinescence (NEN).

Immunoprecipitation of GFP-tagged ALG-1/ALG-2 complexes was performed by pre-clearing worm extract with 50 μL protein-G agarose beads (Roche) per 5 mg total protein for 1 hr at 4° C. The cleared extract was then incubated with 10 μg of monoclonal antibody anti-AFP 3E6 (Qbiogene) for 1 hr at 4° C. followed by 50 μL protein-G agarose. The agarose beads were then washed three times with ice-cold homogenization buffer.

Depletion of let-7 miRNA was monitored by Northern blotting. RNA was eluted from the immobilized 2'-O-methyl oligonucleotide by digestion with 1 mg/ml proteinase K in 200 mM Tris-HCl (pH 7.5), 25 mM EDTA, 300 mM NaCl, 2% (w/v) SDS) at 50° C. for 30 min, followed by extraction with Phenol-Chloroform, and recovered by precipitation with ethanol. Recovered RNA was resuspended in 10 μL formamide loading buffer (98% (v/v) deionized formamide, 10 mM EDTA, 0.025% (w/v) xylene cyanol, 0.025% (w/v) bromophenol blue), heated to 100° C. for 2 min. RNA was resolved on a 15% denaturing acrylamide gel, transferred to Hybond-N membrane (Amersham Biosciences), and detected by Northern analysis using a 5' 32P-radiolabeled anti-sense let-7 RNA probe (UAU ACA ACC UAC UAC CUC AUU; SEQ ID NO: 6) as described (Hutvägner and Zamore, 2002). For in vivo inhibition of let-7 function, 1 mg/ml let-7-complementary 2'-O-methyl oligonucleotide in water (100 μM) and injected into L2 larvae of either wild-type (N2) or lin-41(ma104) strains. let-7 phenotypes were also observed at 10 μM oligonucleotide, but were less penetrant. Phenotypes were scored when the injected animals reached adulthood.

Example 1

Inhibition of RNAi by 2'-O-methyl Oligonucleotides

Although RNAi has proved a straightforward and cost-effective method to assess the function of protein-coding mRNAs (Fire et al., 1998; Caplen et al., 2000; Caplen et al., 2001; Carthew, 2001; Elbashir et al., 2001b) and even some non-coding RNAs (Liang et al., 2003), no comparable method allows the sequence-specific inactivation of the siRNA or miRNA components of the RISC. The invention features such inhibitors. Preferred inhibitors of RISC function are nucleic acid-based molecules that are recognized by the RISC by nucleotide complementarity, but are refractory to RISC-directed endonucleolytic cleavage or translational control. Such molecules are designed such that they are capable of titrating out RISC complexes containing a complementary siRNA or miRNA, but have little or no effect on the function of RISC complexes containing guide RNAs unrelated in sequence. Such RISC inhibitors can further be designed such that they are resistant to degradation by cellular ribonucleases so that they persist long enough to bind RISC and block its function. Finally, inhibitors of small RNA function are designed such that they are capable of acting at concentrations unlikely to elicit non-specific responses to the inhibitor itself, i.e., in the low nanomolar range, the same concentration at which siRNAs themselves are effective.

Figure 1B:
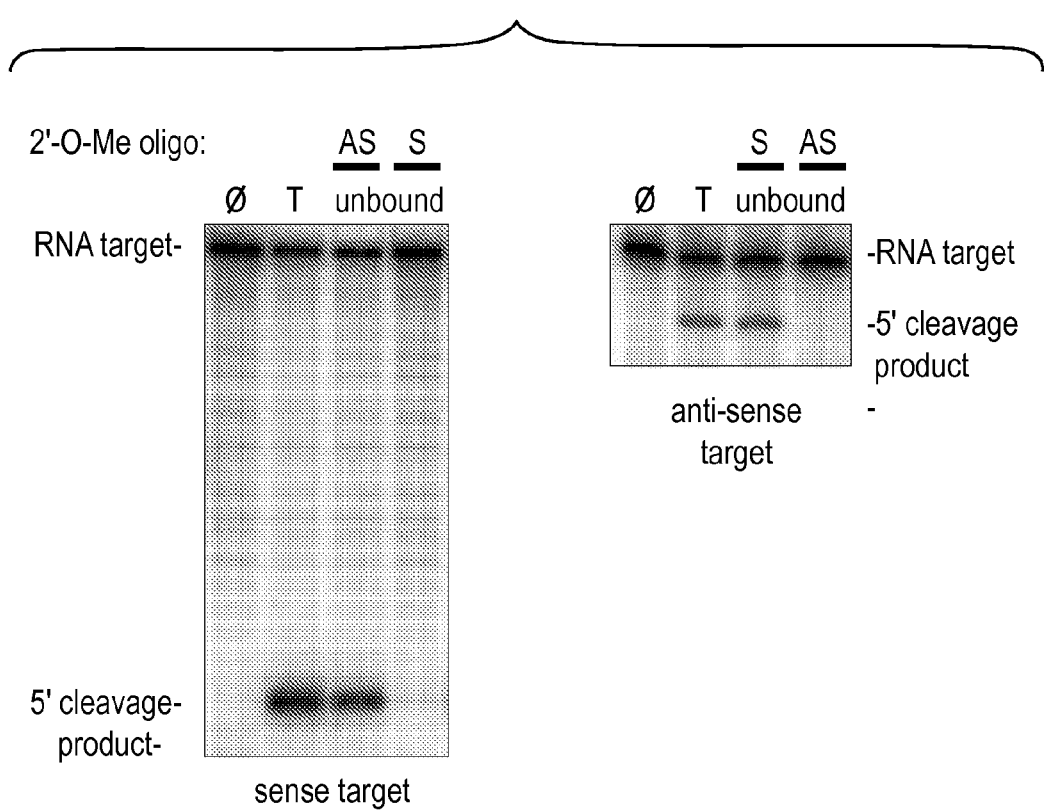
FIG. 1B shows sequence-specific depletion of RNAi activity by immobilized 2'-O-methyl oligonucleotides from *Drosophila* embryo lysate programmed with siRNA. siRNA was incubated with lysate to assemble RISC, then immobilized 2'-O-methyl oligonucleotide was added. Beads were then removed from the supernatant, and either sense or anti-sense $^{32}$P-radiolabeled target RNA was added to the supernatant to measure RISC activity for each siRNA strand. Ø, target RNA before incubation with siRNA-programmed lysate; T, total reaction before depletion; unbound, the supernatant after incubation with the immobilized anti-sense (AS) or sense (S) 2'-O-methyl oligonucleotides shown in FIG. 1A. The absence of 5' cleavage product demonstrated that the sense oligonucleotide depleted RISC containing anti-sense siRNA, but not sense siRNA, and the anti-sense oligonucleotide depleted the sense RISC, but not that containing anti-sense siRNA. Bi, 5' biotin attached via a six-carbon linker.

At micromolar concentration, DNA anti-sense oligonucleotides may block miRNA function in Drosophila embryos (Boutla et al., 2003), but the poor stability of DNA oligonucleotides in vivo may limit their utility. Phosphorothioate substituted DNA oligonucleotides, which show good in vivo stability, do not inhibit RISC function in vitro (data not shown). 2'-O-methyl oligonucleotides are also highly resistant to cellular ribonucleases. To test if 2'-O-methyl oligonucleotides can act as RISC inhibitors, it was examined whether a 2'-O-methyl oligonucleotide, tethered to streptavidin paramagnetic beads via a 5' biotin linkage, could be used to deplete siRNA-programmed RISC from the reaction. Drosophila embryo lysate was programmed with a synthetic siRNA duplex directed against a firefly luciferase (Pp-luc) mRNA target (FIG. 1A). Then, a tethered 31-nucleotide 2'-O-methyl oligonucleotide complementary to the 21 nucleotide siRNA strand was added. Finally, the beads were removed from the solution using a magnet, and the supernatant tested for siRNA-programmed RISC activity. Under these conditions, the 2'-O-methyl oligonucleotide completely depleted the reaction of RISC programmed with the anti-sense strand of the siRNA, but not of RISC programmed with the sense strand (FIG. 1B). Thus, depletion occurred only when the siRNA strand contained within RISC was complementary to the tethered oligonucleotide.

Figure 2:
FIG. 2 shows that 2'-O-methyl oligonucleotides acted as stoichiometric, irreversible inhibitors of RISC function.
Figure 2A:
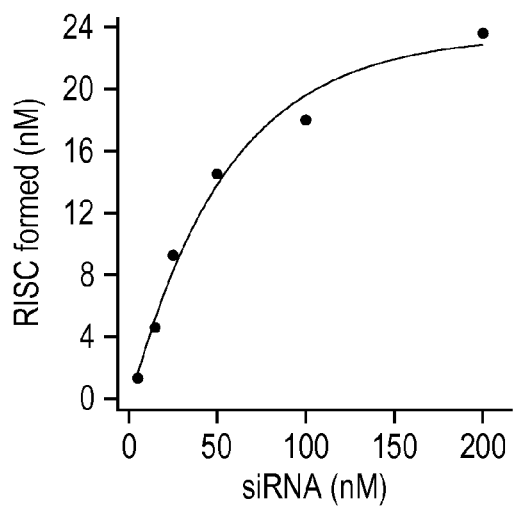
FIG. 2A depicts results of using the immobilized sense 2'-O-methyl oligonucleotide to determine the concentration of $^{32}$P-radiolabeled anti-sense siRNA assembled into RISC in *Drosophila* embryo. The 2'-O-methyl oligonucleotide and siRNA duplex are shown in FIG. 1A.
Figure 2B:
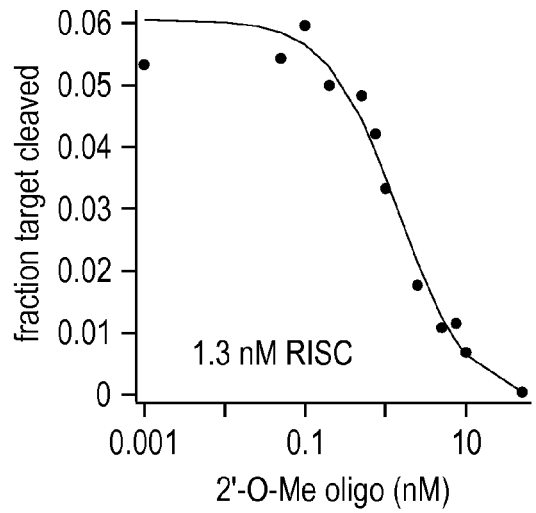
FIG. 2B-2G graphically depict measurement of inhibition of RNAi using free 2'-O-methyl oligonucleotide and 1.3 nM (2B), 4.6 nM (2C), 9.3 nM (2D), 14.5 nM (2E), 18 nM (2F), 23.5 nM (2G) RISC. The concentration of 2'-O-methyl oligonucleotide required for half-maximal inhibition (IC50) was calculated by fitting each data set to a sigmoidal curve using a Hill coefficient of one.
Figure 2C:
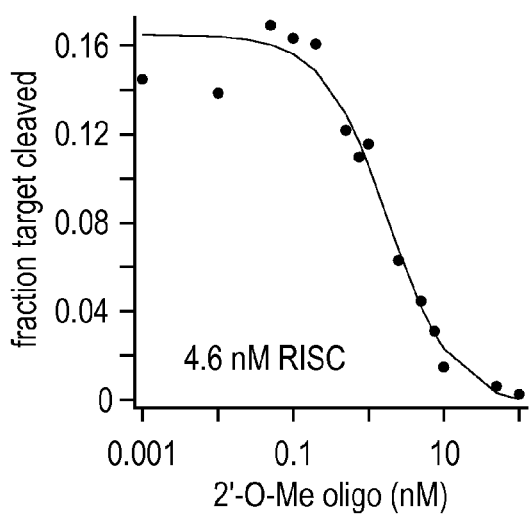
Figure 2D:
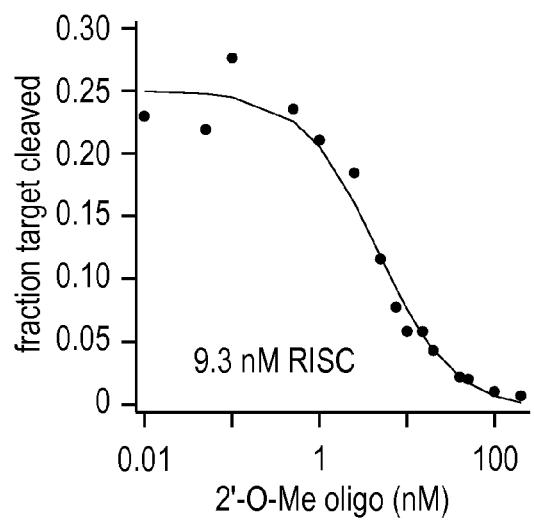
Figure 2E:
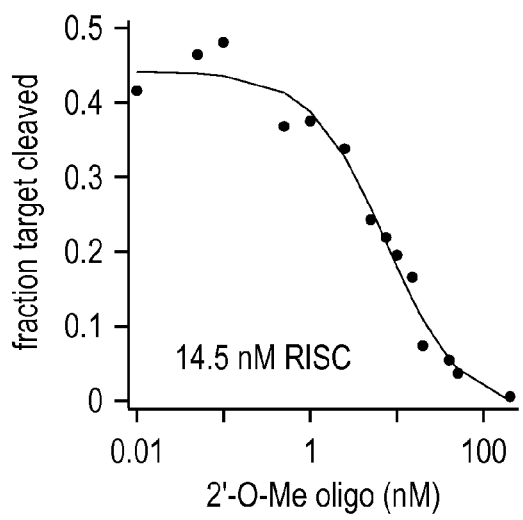
Figure 2F:
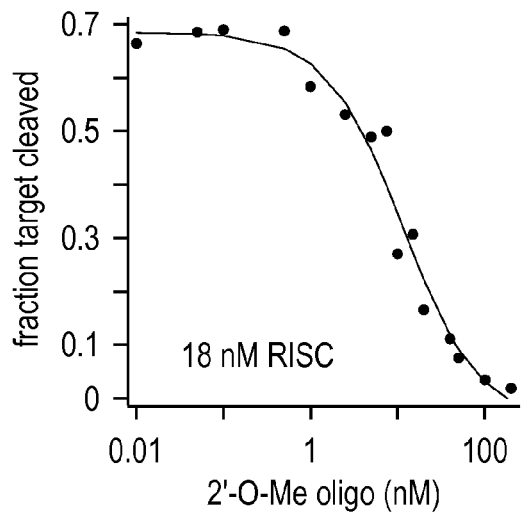
Figure 2G:
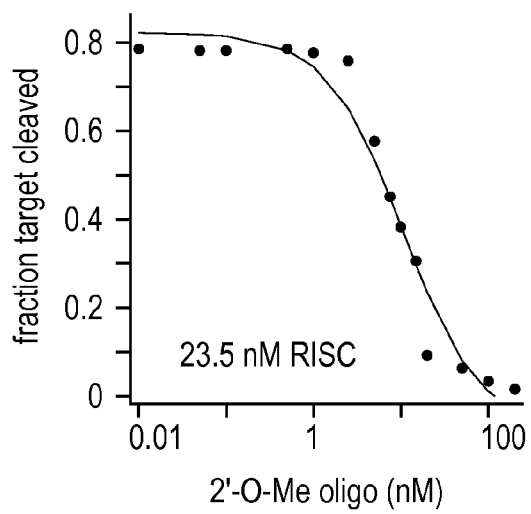

This method was extended to measure the amount of RISC formed in the in vitro reaction at different concentrations of the siRNA duplex. An siRNA duplex in which the anti-sense strand was 5'-$^{32}$P-radiolabeled was incubated in the reaction, then the tethered 2'-O-methyl oligonucleotide added to deplete the reaction of anti-sense siRNA-programmed RISC. The beads were then washed and the fraction of $^{32}$P-siRNA bound to the beads determined. Depletion was verified by testing the supernatant for RISC activity. Formally, the amount of $^{32}$P-siRNA retained on the beads for a given concentration of siRNA duplex places an upper limit on the concentration of RISC formed. However, the presently reported results using this assay were, within error, identical to the amount of RISC measured by two independent methods: the accumulation of single-stranded siRNA from functionally asymmetric siRNA duplexes (Schwarz et al., 2003), and the magnitude of the burst of target cleavage measured by pre-steady state kinetics (data not shown). The simplest explanation for these results was that this assay directly measured siRNA incorporated into RISC. FIG. 2A shows the results of this assay for six different concentrations of siRNA duplex (5, 15, 25, 50, 100, 200 nM siRNA). First, the data show that RISC assembly in vitro was inefficient; the majority of siRNA duplexes did not contribute to RISC production. Second, RISC assembly was saturable, suggesting that some component of RISC itself was limiting.

Figure 2H:
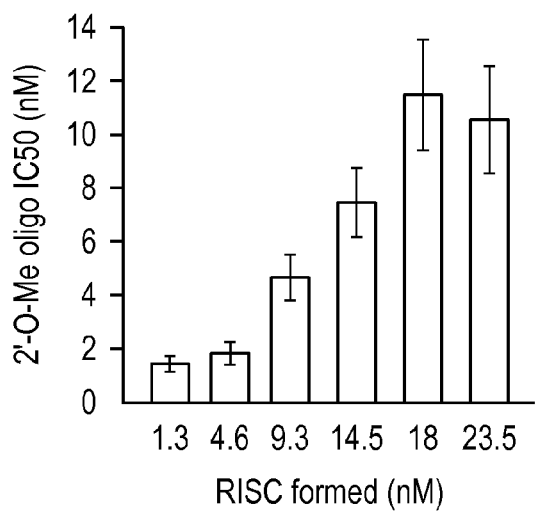
FIG. 2H depicts a plot of IC50 versus RISC concentration, which indicated that each 2'-O-methyl oligonucleotide bound a single RISC. These data also indicated that binding was essentially irreversible.

To understand better the mechanism by which the 2'-O-methyl oligonucleotide interacted with RISC, the concentration of free 2'-O-methyl oligonucleotide required for half-maximal inhibition of RISC activity (IC50; FIGS. 2B-G) was measured at the six different RISC concentrations determined in FIG. 2A. The IC50 for inhibition by free 2'-O-methyl oligonucleotide is show for each RISC concentration in FIG. 2H. The IC50 for the 2'-O-methyl oligonucleotide was remarkably close to half the RISC concentration. These data indicated that a single 31 nucleotide 2'-O-methyl oligonucleotide bound each RISC and blocked its function. Consistent with this apparent 1:1 stoichiometry, the data for the 2'-O-methyl oligonucleotide titrations fit well to sigmoidal curves with a Hill coefficient of 1 (FIG. 2B-G). The sequence specificity of 2'-O-methyl oligonucleotide inhibition of RISC function clearly shows that inhibition reflected binding of the oligo to the RISC. These data are most easily explained if the concentration of the 2'-O-methyl oligonucleotide required for inhibition in these experiments was much greater than the $K_D$ for binding, i.e., the experiments were conducted in a stoichiometric binding regime. Under a stoichiometric binding regime, inhibition by the 2'-O-methyl oligonucleotides would have been essentially irreversible.

Figure 3:
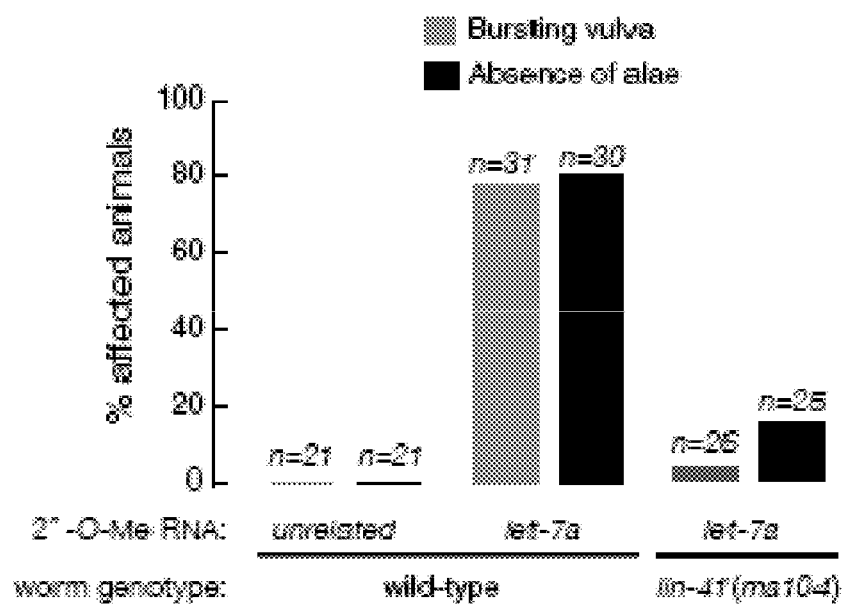
FIG. 3 shows that RISC did not act through an anti-sense mechanism.
Figure 3A:
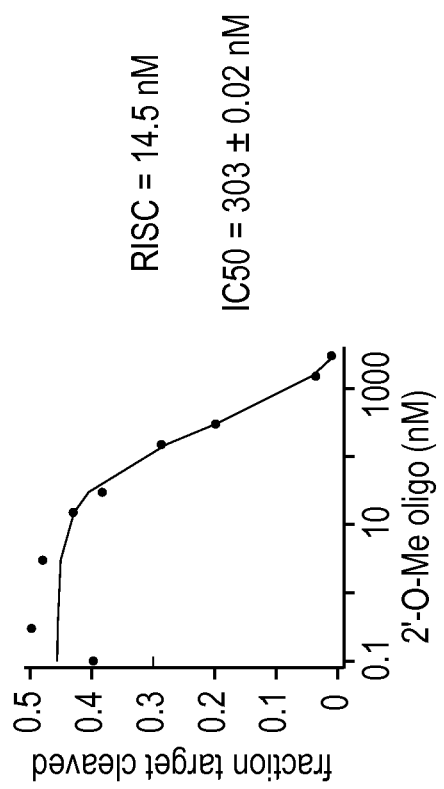
FIG. 3A shows that inhibition of sense-target cleavage by an anti-sense 2'-O-methyl oligonucleotide required ~40-fold higher concentration than by a sense oligonucleotide. The anti-sense oligonucleotide could pair completely with the sense target RNA, but not with the anti-sense siRNA-programmed RISC. The IC50 value and the RISC concentration are indicated. Also shown are the sequences of the sense Pp-luc RNA target (black), the siRNA (red, anti-sense strand; black, sense strand), and the 2'-O-methyl oligonucleotide (blue).
Figure 3B:
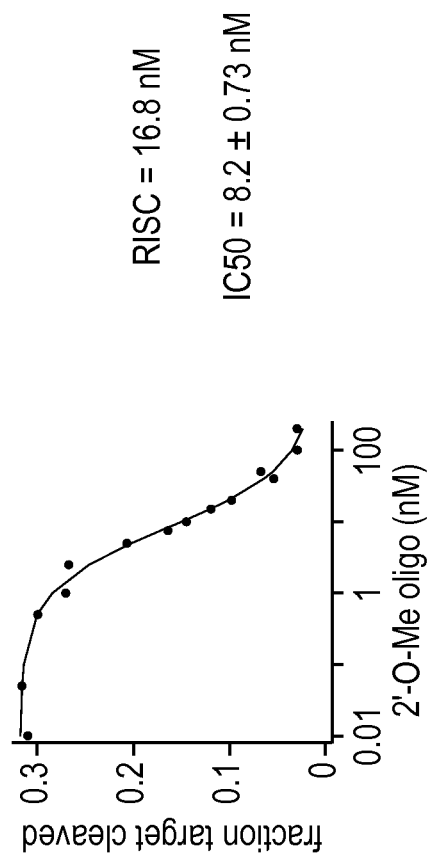
FIG. 3B shows that the same antisense 2'-O-methyl oligonucleotide was an effective competitor of anti-sense target cleavage. In this experiment, inhibition occurred via binding of the anti-sense oligonucleotide to the sense siRNA-programmed RISC, not the target RNA. The IC50 value and the RISC concentration are indicated. Also shown are the sequences of the Pp-luc anti-sense RNA target (black), the siRNA (red, anti-sense strand; black, sense strand) and the 2'-O-methyl oligonucleotide (blue). The G:U wobble in the siRNA duplex in (B) acts to direct the sense-strand into RISC and improve its efficacy in target cleavage.

In theory, the 2'-O-methyl oligonucleotide may have acted by displacing the passenger (sense) strand of the siRNA duplex, thereby blocking incorporation of the guide (anti-sense) strand into RISC (Elbashir et al., 2001c). This possibility can be excluded because a 5' tethered 31 nucleotide 2'-O-methyl oligonucleotide complementary to the passenger strand of the siRNA did not deplete guide-strand RISC activity (FIG. 1B). Similarly, an anti-sense sequence 2'-O-methyl oligonucleotide could not pair with anti-sense RISC, but could pair with a sense target mRNA. This anti-sense 2'-O-methyl oligonucleotide was anticipated to pair with the sense target mRNA and occlude the anti-sense RISC from the target. Surprisingly, this anti-sense 2'-O-methyl oligonucleotide was a poor inhibitor of anti-sense RISC function when it was used to bind the target site, requiring 300 nM for half-maximal inhibition in a reaction containing 14.5 nM RISC and 3 nM sense target RNA (FIG. 3A). By contrast, the same anti-sense 2'-O-methyl oligonucleotide was highly effective in blocking the activity of the sense RISC, to which it was complementary, acting with an IC50 of 8.2 nM in a reaction containing 16.8 nM sense-strand RISC and 3 nM anti-sense target RNA (FIG. 3B). (In this experiment, sense-strand RISC was generated by changing the first nucleotide of the sense-strand from C to U, thereby reversing the functional asymmetry (Schwarz et al., 2003).)

Thus, the interaction of 2'-O-methyl oligonucleotide with RISC was dramatically different from the interaction of 2'-O-methyl oligonucleotide with target RNA; RISC had a more than 40-fold greater affinity for the 2'-O-methyl oligonucleotide than the oligonucleotide had for the RNA target (compare FIGS. 2E and 3A). These data indicated that the interaction of RISC with target was not driven by simple nucleic acid hybridization. Inhibition of the siRNA-programmed RISC by a 2'-O-methyl oligonucleotide with the sequence of the target RNA was more effective than inhibition mediated by binding of an oligonucleotide to the target RNA itself. Thus, the RISC was more adept at finding and/or remaining bound to the target RNA than a 2'-O-methyl oligonucleotide. These data indicated that specific proteins in the RISC facilitated either target finding, target binding, or both. Consistent with this idea, inhibition of RISC function was incomplete using 21 nucleotide 2'-O-methyl oligonucleotides (data not shown). Thus, target sequence flanking the site of complementarity to the siRNA guide strand likely plays a role in target-RISC binding. An active mechanism that involves target sequences flanking the siRNA may facilitate the search for the target sequence.

Example 2

Inhibition of RNAi in Cultured Human Cells

The data presented in Example 1 showed that 2'-O-methyl oligonucleotides were stoichiometric, irreversible, sequence-specific inhibitors of siRNA function in RNAi reactions using Drosophila embryo lysate. To address the question of whether 2'-O-methyl oligonucleotides could block siRNA function in vivo, sequential transfection experiments were performed using 1, 5, 10 or 25 nM siRNA duplex. siRNA was transfected on the first day, then reporter and control plasmids cotransfected together with various amounts of 2'-O-methyl oligonucleotide on the second day. Silencing of Pp-luc, relative to the Rr-luc control was measured on the third day. For each siRNA concentration, the concentration of 2'-O-methyl oligonucleotide required for half-maximal inhibition of RNAi was determined (FIG. 4A-D). Increasing amounts of the 2'-O-methyl oligonucleotide gradually extinguished the ability of the siRNA to silence Pp-Luc in all four experiments. The inhibition of silencing in the cultured cells could not have been a consequence of the 2'-O-methyl oligonucleotide displacing the sense strand of the siRNA duplex, because assembly of siRNA into RISC occurred a full day before the oligonucleotide was introduced. When 10 nM siRNA was used in the transfection, ~1 nM 2'-O-methyl RNA was required for half-maximal inhibition of RNAi (FIGS. 4C and E). At 25 nM siRNA, approximately 1.1 nM 2'-O-methyl RNA was required to inhibit half the RNAi activity (FIGS. 4D and E). In FIG. 4E, siRNA concentration was plotted versus the amount of 2'-O-methyl oligonucleotide required for half-maximal inhibition of silencing (IC50). The data fit well to a sigmoidal curve, consistent with the idea that, at these concentrations, increasing amounts of siRNA did not produce a corresponding increase in RISC activity. Higher concentrations of siRNA could not be examined because they produced sequence-independent changes in gene expression (Persengiev et al., 2003; Semizarov et al., 2003). It was thus concluded that both cells and extracts had a limited capacity to assemble RISC on exogenous siRNA. These data indicated that the use of siRNA concentrations greater than that required to produce the maximum amount of RISC would lead to the accumulation of double-stranded siRNA in vivo, and may thus contribute to undesirable, sequence non-specific responses sometimes observed in cultured mammalian cells (Sledz et al., 2003).

Example 3

Inhibition of miRNA Function In Vitro and In Vivo

Figures 5A, 5B:
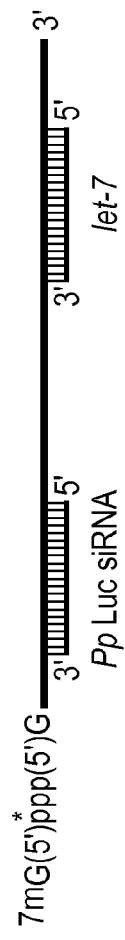
FIG. 5A shows the sequence of the let-7 complementary site in the target RNA (black), of the siRNA (red, anti-sense strand; black, sense strand) and of the let-7-complementary 2'-O-methyl oligonucleotide (blue).
FIG. 5B depicts a schematic representation of the target RNA, which contained both Pp-luc and anti-sense let-7 sequences. The left lanes of FIG. 5C show the result of an experiment in which *Drosophila* embryo lysate was programmed with let-7 siRNA, then the target RNA and the 2'-O-methyl oligonucleotide were added together. The right lanes of FIG. 5C show the result obtained by adding target RNA and 2'-O-methyl oligonucleotide to HeLa S100 extract, which contains endogenous human let-7-programmed RISC.
Figure 5D:
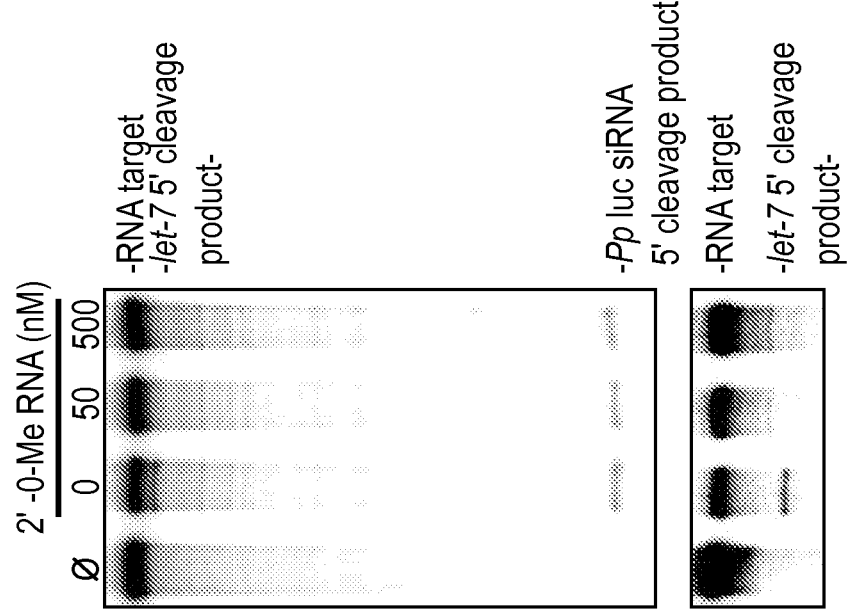
FIG. 5D shows that an RNA target containing both Pp-luc and anti-sense let-7 sequence could be simultaneously targeted by Pp-luc siRNA and endogenous let-7 in HeLa S100 lysate. The let-7-complementary 2'-O-methyl oligonucleotide blocked let-7-, but not Pp-luc siRNA-, programmed RISC function. The lower panel shows the same samples analyzed separately to resolve better the let-7 5'cleavage product.
Figure 5C:
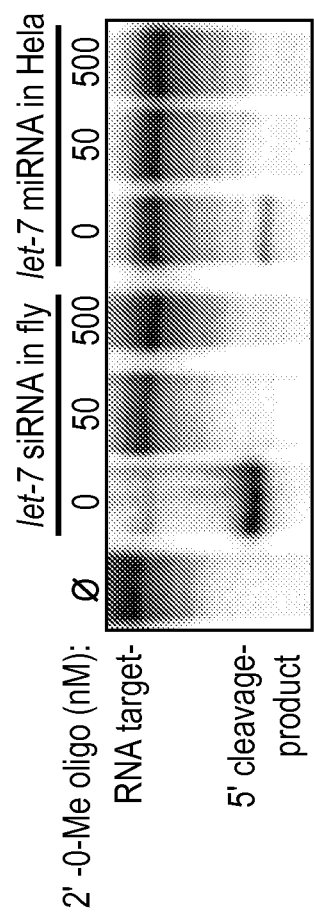
FIG. 5 depicts that a complementary 2'-O-methyl oligonucleotide blocked endogenous let7-containing RISC function.
In FIG. 5E, *Drosophila* embryo lysate was programmed with let-7 siRNA and then incubated with biotinylated 2'-O-methyl oligonucleotide tethered to paramagnetic streptavidin beads. The beads were removed and the supernatant tested for RNAi activity. Ø, target RNA before incubation with siRNA-programmed lysate; T, total reaction before depletion; unbound, the supernatant after incubation with the paramagnetic beads. 'Mock' indicates no oligonucleotide was used on the beads; 'let-7' indicates that the beads contained the let-7-complementary oligonucleotide shown in FIG. 5A.
Figure 5E:
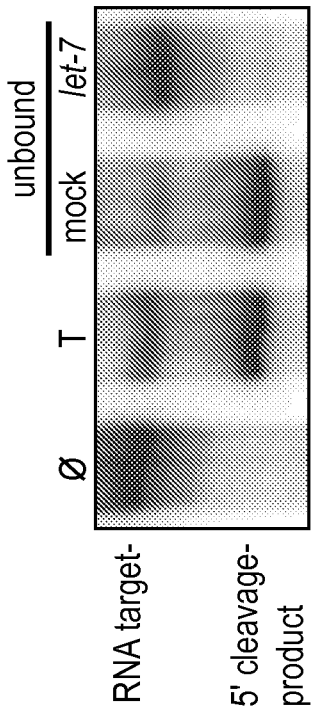
Figure 6A:
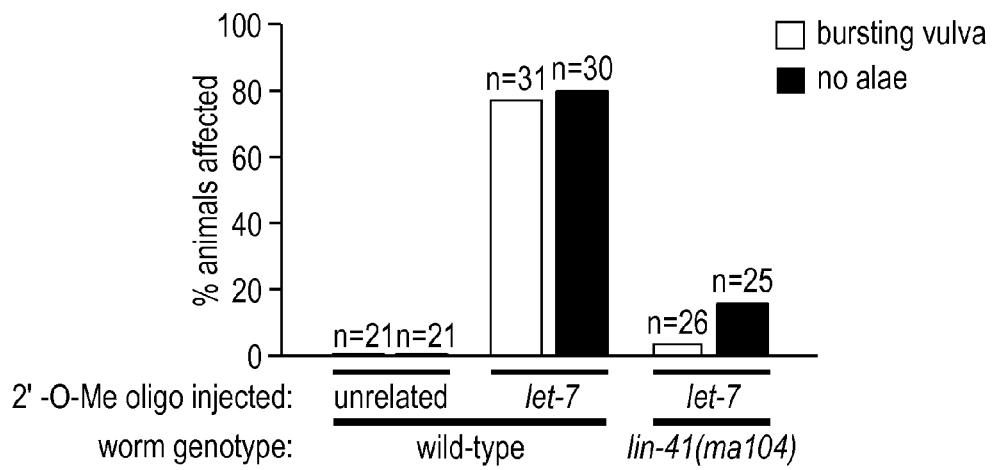
In FIG. 6A, wild-type and lin-41(ma104) L2 stage *C. elegans* larvae were injected with either a 2'-O-methyl oligonucleotide complementary to let-7 miRNA (FIG. 5A) or an unrelated Pp-luc 2'-O-methyl oligonucleotide. Absence of alae and presence of bursting vulvae were scored when the injected animals reached adulthood.

In animal cells, miRNAs are thought predominantly to function as translational regulators. Nonetheless, a growing body of evidence suggests that they function through a similar, if not identical, RISC as siRNAs (Hutvägner and Zamore, 2002; Zeng et al., 2002; Doench et al., 2003; Khvorova et al., 2003; Schwarz et al., 2003; Zeng et al., 2003b). Because 2'-O-methyl oligonucleotides blocked siRNA function in vitro and in cultured human cells, it was asked if these oligonucleotides might likewise disrupt the function of a specific miRNA in vitro and in vivo. An ideal candidate for such an miRNA is let-7. Classical genetic mutations in C. elegans let-7 produce well characterized, readily scored phenotypes. Furthermore, human HeLa cells express multiple let-7 family members (Rfam Accession numbers MI0000060-MI0000068, MI0000433 and MI0000434), and endogenous let-7 is present naturally in RISC (Hutvägner and Zamore, 2002; *Zeng and Cullen,* 2003). A 31 nucleotide 2'-O-methyl oligonucleotide complementary to let-7 was tested for the ability to block target cleavage guided by the endogenous let-7-programmed RISC present in HeLa S100 extract (FIG. 5A). (The assay detected the target-cleaving activity of let-7; endogenous human mRNA targets whose translation may be repressed by let-7 have not yet been tested.) As a control, the oligonucleotide was tested for the ability to block the activity of a let-7-containing RISC assembled in vitro in Drosophila embryo lysate. Addition of this 2'-O-methyl oligonucleotide efficiently blocked target RNA cleavage directed by the endogenous let-7-programmed RISC in the HeLa S100 extract and by the RISC programmed with exogenous let-7 siRNA duplex in Drosophila embryo lysate (FIG. 5C). In addition to containing endogenous let-7-programmed RISC, HeLa S100 can be programmed with exogenous siRNA duplexes (Martinez et al., 2002; Schwarz et al., 2002). The target RNA used in FIG. 5B also contained sequence from the Pp-luc mRNA, and could therefore be targeted by a Pp-lucspecific siRNA duplex (FIGS. 1A and 5C). The Pp-luc siRNA duplex was incubated with the human HeLa S100 extract to form Pp-luc-directed RISC. let-7-complementary 2'-O-methyl oligonucleotide and the target RNA were then added. The oligonucleotide blocked cleavage by the endogenous let-7-programmed RISC, but had no effect on cleavage directed by the exogenous Pp-luc siRNA in the same reaction (FIG. 5D). When tethered to a paramagnetic bead, this oligonucleotide could also quantitatively deplete the let-7-programmed RISC from the *Drosophila* embryo lysate (FIG. 5E), demonstrating that, again, the interaction between the 2'-O-methyl oligonucleotide and the RISC was apparently irreversible. The 2'-O-methyl oligonucleotide was a specific and potent inhibitor of target cleavage directed by a naturally occurring, miRNA-programmed RISC. Furthermore, these data demonstrated that individual RISC complexes acted independently even when they targeted the same RNA. Next, 2'-O-methyl oligonucleotides were tested for the ability to inhibit miRNA function in vivo. Translational repression directed by miRNAs occurs in *C. elegans*, where both the lin-4 and let-7 miRNAs have been shown to block translation of their target mRNAs without altering mRNA stability (Wightman et al., 1993; Ha et al., 1996; Moss et al., 1997; *Olsen and Ambros*, 1999; Reinhart et al., 2000; Seggerson et al., 2002). The genetics of lin-4 and let-7 function are well characterized in worms, where they are required during larval development to control the timing and pattern of cell division in the hypodermis (Lee et al., 1993; Reinhart et al., 2000). First, 2'-O-methyl oligonucleotides complementary to either lin-4 or let-7 were injected into the germline of wild-type adult hermaphrodites to examine whether the RISC inactivators could block lin-4 or let-7 function during the larval development of the resulting progeny. Although the 2'-O-methyl oligonucleotides were not toxic, and when coinjected with an unrelated DNA transformation reporter did not prevent the uptake and expression of the coinjected DNA, inhibition of lin-4 or let-7 activity was not observed (data not shown). This finding indicated that single stranded 2'-O-methyl oligonucleotides were not efficiently transmitted to the progeny of injected animals. To circumvent this problem, 2'-O-methyl oligonucleotides were injected directly into larvae and phenotypes of the injected animals were examined. The lin-4 miRNA functions in L1/L2 larvae and the inventors have found that L1 larvae do not survive microinjection (data not shown), thus it was not possible to assay for inhibition of lin-4 function by direct injection. In contrast, let-7 functions during the L4 stage, and L2 and L3 larvae were found to survive the microinjection procedure (See Experimental Procedures). Loss of let-7 function causes worms to reiterate the L4 larval molt and inappropriately produce larval cuticle at the adult stage. Loss-of-function let-7 phenotypes include weak cuticles prone to bursting at the vulva, defects in egg-laying, and loss of adult-specific cuticular structures that run the length of the animal's body, the alae (Reinhart et al., 2000). After larvae were injected with the let-7-specific 2'-Omethyl oligonucleotide, 80% of the adult worms lacked alae; 77% lacked alae and also exhibited bursting vulvae (FIG. 6A). In contrast, animals injected with an unrelated control 2'-O-methyl oligonucleotide displayed no abnormal phenotypes (FIG. 6A). All of the phenotypes associated with injection of the let-7 complementary 2'-O-methyl oligonucleotide were consistent with a loss of let-7 activity. let-7 represses translation of lin-41 (Locus link ID 172760) mRNA by binding to a partially complementary site in the lin-41 3' untranslated region (Reinhart et al., 2000; Slack et al., 2000; Vella et al., 2004). Consequently, many of the phenotypes associated with the loss of let-7 reflect overexpression of LIN-41 protein; let-7 mutants are partially suppressed by mutations in lin-41. It was reasoned that if the phenotypes observed in the injected larvae reflected a loss of let-7 activity, then they should likely be partially suppressed by a lin-41 mutation (Reinhart et al., 2000; Slack et al., 2000). To test this possibility, the let-7-specific 2'-O-methyl oligonucleotide was injected into the lin-41(ma104) strain and penetrance of phenotypes was compared with an injected wild-type population. Consistent with the idea that the injected oligonucleotide specifically inactivates let-7, the absence of alae and vulval bursting phenotypes were both suppressed in the lin-41(ma104) mutant strain (FIG. 6A). The number of worms lacking alae was reduced from 80% to 16%, and worms with bursting vulvae were dramatically reduced (74% in wild-type compared to 3.8% in lin-41(ma104) strain). The observed suppression (64%) was nearly identical to that reported for a let-7, lin-41 genetic double mutant (70%; Reinhart et al., 2000; Slack et al., 2000). Together, these data support the idea 2'-O-methyl oligonucleotides can act as potent inhibitors of miRNA function in vivo and can further be used to probe the function of specific miRNAs in vivo.

Example 4

Isolation of Protein-miRNA Complex Using a Tethered 2'-O-Methyl Oligonucleotide

Figure 6B:
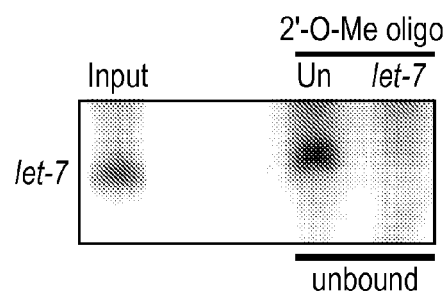
FIG. 6B depicts isolation of let-7-associated proteins with a tethered 2'-O-methyl oligonucleotide. Northern analysis of let-7 miRNA remaining in the supernatant of the worm lysate after incubation with the let-7-complementary (let-7) or Pp-luc (unrelated) oligonucleotide is shown. Input represented the equivalent of 50% of the total extract incubated with tethered oligonucleotide.
Figure 6D:
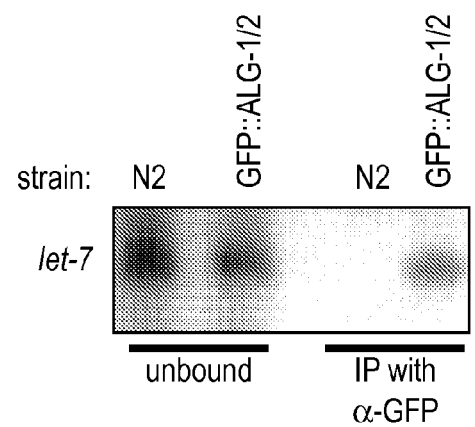
FIG. 6D depicts Northern analysis of let-7 miRNA in ALG-1/ALG-2 complexes. Extracts prepared from mixed stage wild-type worms (N2), or GFP::ALG-1/ALG-2 transgenic worms, were immunoprecipitated using anti-GFP monoclonal antibodies. The unbound and immunoprecipitated RNAs were analyzed by Northern hybridization for let-7 and, in FIG. 6E, 5% of the immunoprecipitated protein was analyzed by Western blotting for GFP to confirm recovery of the GFP-tagged ALG1/2 proteins.
Figure 6C:
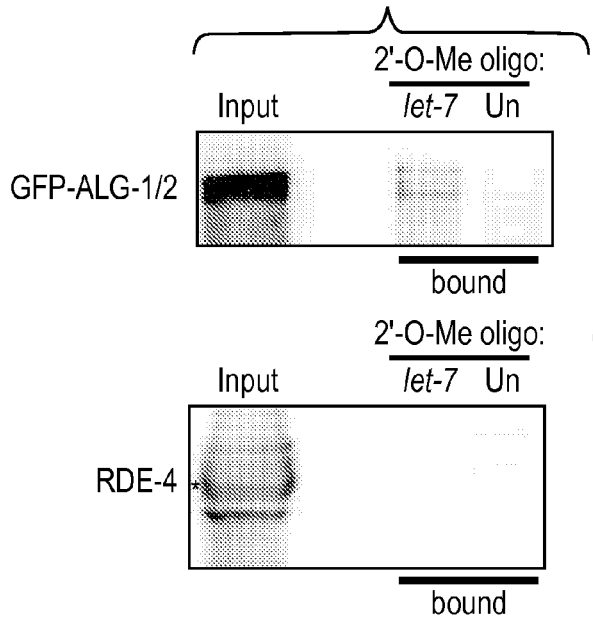
FIG. 6C depicts Western blot analysis of the GFP-tagged ALG-1 and ALG-2 proteins associated with let-7. Extracts from a transgenic strain expressing the tagged proteins were incubated with the indicated tethered 2'-O-methyl oligonucleotide, then the beads were washed and bound proteins fractionated on an 8% polyacrylamide/SDS gel. Western blots were probed using anti-GFP monoclonal or anti-RDE-4 polyclonal antibody. The RDE-4-specific band is marked with an asterisk (Tabara et al., 2002).

The in vitro experiments presented above indicated that both siRNA- and miRNA-containing RISCs were stably bound by 2'-O-methyl oligonucleotides. It was next tested whether tethered 2'-O-methyl oligonucleotides could be used to isolate cellular factors associated with specific miRNAs. In human cells, miRNAs such as let-7 have been identified to occupy a protein complex that contains Argonaute proteins (Hutvägner and Zamore, 2002; Mourelatos et al., 2002; Dostie et al., 2003). In *C. elegans*, the Argonaute protein-encoding genes alg-1 and alg-2 were shown to be required for the biogenesis and/or function of the miRNAs lin-4 and let-7 (Grishok et al., 2001), but it was not shown if ALG-1 and ALG-2 proteins were directly associated with let-7. Extracts were prepared from wild-type adult worms carrying a transgene expressing GFP-tagged ALG-1 and ALG-2 proteins. The extracts were then incubated with the let-7-complementary 2'-O-methyl oligonucleotide tethered by a 5' biotin to streptavidin-conjugated paramagnetic beads. As a control, the experiment was performed in parallel using an oligonucleotide not complementary to let-7. The let-7 complementary, but not the control, oligonucleotide depleted nearly all the let-7 miRNA from the extract (FIG. 6B). Western blotting using anti-GFP antibody revealed that both GFP-tagged ALG-1 and ALG-2 protein co-purified with the let-7-complementary oligonucleotide, but not the control oligonucleotide (FIG. 6C). In contrast, the RNA binding protein, RDE-4 (Locus link ID 176438), which is required for RNAi but not for miRNA function in *C. elegans*, did not co-purify with the let-7 complementarity oligonucleotide, providing further support for the specificity of the let-7:ALG-1/ALG-2 interaction (FIG. 6C).

Figure 6E:
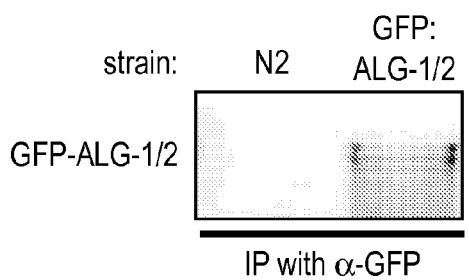
FIG. 6 shows that injection of a 2'-O-methyl oligonucleotide complementary to let-7 miRNA could phenocopy the loss of let-7 function in *C. elegans*.

Finally, coimmunoprecipitation assay was employed to examine the interaction between let-7 and ALG-1/ALG-2. In this assay, a monoclonal anti-GFP antibody was used to co-immunoprecipitate ALG-1/ALG-2 small RNAs from the GFP::ALG-1/GFP::ALG-2 strain, which expressed GFP-ALG-1/ALG-2 fusion proteins (FIG. 6E). Northern analysis of the immune complex showed that it contained mature 22 nucleotide let-7 miRNA (FIG. 6D). No detectable let-7 was recovered with the anti-GFP antibody from the N2 wild-type strain. By comparing the fraction of let-7 associated with GFP::ALG-1/ALG-2 with the unbound fraction of let-7 miRNA, it was estimated that approximately 30% of the 22 nucleotide let-7 RNAs co-immunoprecipitated with GFP::ALG-1 and GFP::ALG-2. These data support a model in which ALG-1 and ALG-2 form a complex, in vivo, that contains a substantial fraction of the mature let-7 miRNA.

Example 5

Identification of let-7-Regulated Transcripts

Figure 7A:
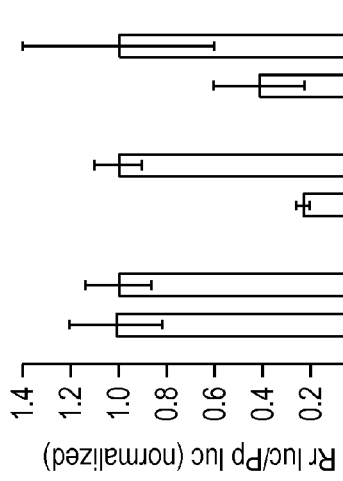
FIG. 7A shows by Northern blot that the let-7 gene family was expressed in HeLa cells and differentiated NT2N cells but not in undifferentiated NT2 cells.
Figure 7B:
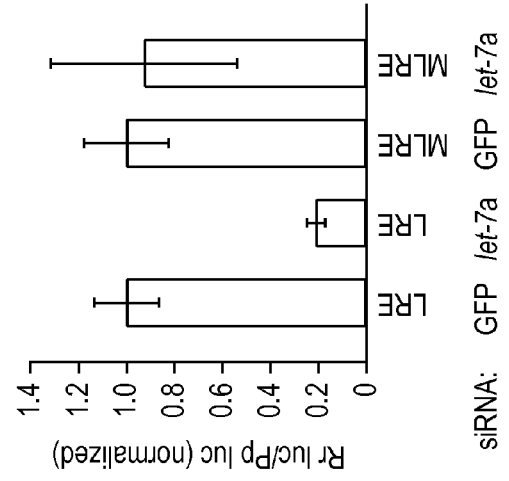
FIG. 7B shows that the activity of a Luciferase reporter plasmid containing let-7 responsive element (LRE) was repressed in the let-7 expressing cell lines. (MLRE was a control Luciferase gene containing scrambled let-7 responsive element that was not sensitive to let-7-mediated repression.)
Figure 7C:
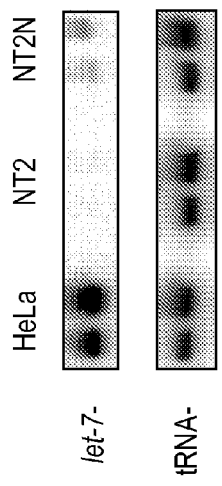
FIG. 7C depicts that 2'-O-methyl oligonucleotides were potent inhibitors of let-7 in HeLa cells.
Figure 7D:
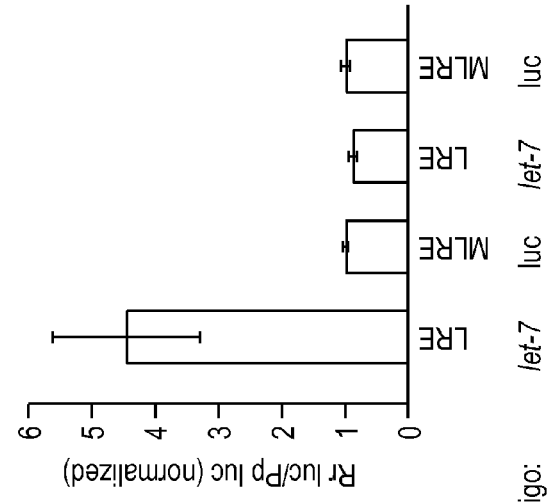
FIG. 7D shows that exogenous let-7 regulated the expression of the LRE containing reporter gene.

Use of 2'-O-methyl oligonucleotides designed to inhibit human let-7 enabled identification and characterization of target genes and pathways which are regulated by the human let-7 miRNA family. An experimental system was developed based on two human cell lines. HeLa cells exhibited high levels of let-7 expression and presented an ideal subject for let-7 inhibition studies, whereas undifferentiated NT2 cells did not express the let-7 gene family and presented a cell type in which let-7 could be transiently "over-expressed" by transfecting it as an siRNA into the cells (FIG. 7A). Inhibition and over-expression of let-7 were monitored in these respective cell types using a sensor target plasmid containing a let-7 complementary site, which controls luciferase expression. Inhibition of let-7 in HeLa cells produced a several-fold increase in luciferase expression, while expression of let-7 in NT2 cells resulted in a several-fold decrease in luciferase expression (FIGS. 7B, C, D).

Human gene expression profiles were assessed for both let-7 inhibitor-treated and untreated HeLa cells, and for let-7 treated NT2 cells using microarrays. mRNAs whose expression was reduced in the let-7 expressing cells (NT2 cells) and/or induced in the let-7 suppressed cells (HeLa cells) were identified. Two genes, HMGA2 and Dicer, were both significantly induced in HeLa cells upon let-7 inhibition using 2'-O-methyl oligonucleotides and were significantly repressed in NT2 cells as a consequence of let-7 transfection. Additionally, several genes were identified in which expression was affected by inhibition or induction of let-7 (FIG. 8A). Many of these mRNAs, including HMGA2 and Dicer, contain predicted multiple let-7 recognition elements. For HMGA2 and Dicer, the microarray data were confirmed for transcript and protein expression effects using real-time PCR and western blot analysis (FIGS. 8B, C; FIG. 9).

These data demonstrate the powerful, effective use of 2'-O-methyl oligonucleotides to identify miRNA targets through direct, sequence-specific inhibition of miRNA function. Transiently expressed miRNA (transfected as an siRNA) was also demonstrated to regulate its natural target mRNAs. Further, it has now been shown that induction or inhibition of a miRNA produced significant changes in the expression of the target mRNA, which could be readily scored using expression profiling.

REFERENCES

Ambros, V., et al. (2003). Curr Biol 13, 807-818.
Aravin, A. A., et al. (2003). Dev Cell 5, 337-350.
Bernstein, E., et al. (2001). Nature 409, 363-366.
Boutla, A., Delidakis, C., and Tabler, M. (2003). Nucleic Acids Res 31, 4973-4980.
Brennecke, J., and Cohen, S. (2003). Genome Biol 4, 228.
Brennecke, J., et al. (2003). Cell 113, 25-36.
Caplen, N. J., et al. (2000). Gene 252, 95-105.
Caplen, N. J., et al. (2001). Proc Natl Acad Sci USA 98, 9742-9747.
Carthew, R. W. (2001). Curr Opin Cell Biol 13, 244-248.
Catalanotto, C., et al. (2000). Nature 404, 245.
Catalanotto, C., et al. (2002). Genes Dev 16, 790-795.
Caudy, A. A., et al. (2002). Genes Dev 16, 2491-2496.
Cogoni, C., and Macino, G. (1997). Proc Natl Acad Sci USA 94, 10233-10238.
Cogoni, C., and Macino, G. (1999a). Nature 399, 166-169.
Cogoni, C., and Macino, G. (1999b). Science 286, 2342-2344.
Conte, D., and Mello, C. C. (2003). In Current Protocols in Molecular Biology, F. M.
Asubel et al., eds. (John Wiley and & Sons), pp. 26.23.21-26.23.20.
Dalmay, T., et al. (2000). Cell 101, 543-553.
Dalmay, T., et al. (2001). EMBO J. 20, 2069-2078.
Doench, J. G., Petersen, C. P., and Sharp, P. A. (2003). Genes Dev 17, 438-442.
Dostie, J., et al. (2003). RNA 9, 180-186.
Elbashir, S. M., et al. (2001a). Nature 411, 494-498.
Elbashir, S. M., Lendeckel, W., and Tuschl, T. (2001b). Genes Dev 15, 188-200.
Elbashir, S. M., et al. (2001c). EMBO J. 20, 6877-6888.
Enright, A., et al. (2003). Genome Biol 5, Epub 2003 Dec. 12.
Fagard, M., et al. (2000). Proc. Natl. Acad. Sci. USA 97, 11650-11654.
Fire, A., et al. (1998). Nature 391, 806-811.
Grishok, A., and Mello, C. C. (2002). Adv Genet. 46, 339-360.
Grishok, A., et al. (2001). Cell 106, 23-34.
Grishok, A., Tabara, H., and Mello, C. (2000). Science 287, 2494-2497.
Ha, I., Wightman, B., and Ruvkun, G. (1996). Genes Dev 10, 3041-3050.
Haley, B., Tang, G., and Zamore, P. D. (2003). Methods 30, 330-336.
Hammond, S. M., et al. (2001a). Science 293, 1146-1150.
Hammond, S. M., Caudy, A. A., and Hannon, G. J. (2001b). Nat Rev Genet. 2, 110-119.
Hutvágner, G., et al. (2001). Science 293, 834-838.
Hutvágner, G., and Zamore, P. D. (2002). Science 297, 2056-2060.
Ketting, R. F., et al. (2001). Genes Dev 15, 2654-2659.
Ketting, R. F., et al. (1999). Cell 99, 133-141.
Ketting, R. F., and Plasterk, R. H. (2000). Nature 404, 296-298.
Khvorova, A., Reynolds, A., and Jayasena, S. D. (2003). Cell 115, 209-216.
Knight, S. W., and Bass, B. L. (2001). Science 293, 2269-2271.
Lagos-Quintana, M., et al. (2001). Science 294, 853-858.
Lagos-Quintana, M., et al. (2002). Curr. Biol. 12, 735-739.
Lagos-Quintana, M., et al. (2003). RNA 9, 175-179.
Lau, N. C., Lim, L. P., Weinstein, E. G., and Bartel, D. P. (2001). Science 294, 858-862.
Lee, R. C., and Ambros, V. (2001). Science 294, 862-864.
Lee, R. C., Feinbaum, R. L., and Ambros, V. (1993). Cell 75, 843-854.
Lewis, B., et al. (2003). Cell 115, 787-798.
Liang, X. H., Liu, Q., and Michaeli, S. (2003). Proc. Natl. Acad. Sci. USA 100, 7521-7526.
Lim, L. P., et al. (2003a). Science 299, 1540.
Lim, L. P., et al. (2003b). Genes Dev 17, 991-1008.
Liu, Q., et al. (2003). Science 301, 1921-1925.
Martinez, J., et al. (2002). Cell 110, 563-574.
Moss, E. G., Lee, R. C., and Ambros, V. (1997). Cell 88, 637-646.
Mourelatos, Z., et al. (2002). Genes Dev 16, 720-728.

Mourrain, P., et al. (2000). Cell 101, 533-542.
Nykänen, A., Haley, B., and Zamore, P. D. (2001). Cell 107, 309-321.
Olsen, P. H., and Ambros, V. (1999). Dev Biol 216, 671-680.
Persengiev, S. P., Zhu, X., and Green, M. R. (2003). RNA 10, 12-18.
Poy, M. N., et al. (2004). Nature 432, 226-230.
Reinhart, B. J., et al. (2000). Nature 403, 901-906.
Reinhart, B. J., et al. (2002). Genes Dev 16, 1616-1626.
Saxena, S., Jonsson, Z. O., and Dutta, A. (2003). J Biol Chem 278, 44312-44319.
Schwarz, D. S., et al. (2003). Cell 115, 199-208.
Schwarz, D. S., et al. (2002). *Molecular Cell* 10, 537-548.
Seggerson, K., Tang, L., and Moss, E. G. (2002). Dev Biol 243, 215-225.
Semizarov, D., et al. (2003). Proc Natl Acad Sci USA 100, 6347-6352.
Slack, F. J., et al. (2000). Mol Cell 5, 659-669.
Sledz, C. A., et al. (2003). Nat Cell Biol 5, 834-839.
Stark, A., Brennecke, J., Russel, R., and Cohen, S. (2003). PLoS Biology 1, 1-13.
Tabara, H., et al. (1999). Cell 99, 123-132.
Tabara, H., Yigit, E., Siomi, H., and Mello, C. C. (2002). Cell 109, 861-871.
Tang, G., Reinhart, B. J., Bartel, D. P., and Zamore, P. D. (2003). Genes Dev 17, 49-63.
Tijsterman, M., et al. (2002a). Science 295, 694-697.
Tijsterman, M., et al. (2002b). Curr Biol 12, 1535-1540.
Tuschl, T., et al. (1999). Genes Dev 13, 3191-3197.
Vella, M., et al. (2004). Genes Dev 18, 132-137.
Wightman, B., Ha, I., and Ruvkun, G. (1993). Cell 75, 855-862.
Wu-Scharf, D., et al. (2000). Science 290, 1159-1163.
Xu, P., et al. (2003). Curr Biol 13, 790-795.
Zamore, P. D., et al. (2000). Cell 101, 25-33.
Zeng, Y., Wagner, E. J., and Cullen, B. R. (2002). Molecular Cell 9, 1327-1333.
Zeng, Y., and Cullen, B. R. (2003a). RNA 9, 112-123.
Zeng, Y., Yi, R., and Cullen, B. R. (2003b). Proc Natl Acad Sci USA 100, 9779-9784.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting RNA silencing of a gene, comprising, contacting a mammalian cell or organism containing an exogenous siRNA duplex that directs RNA silencing of the gene by RISC-mediated cleavage, with a single-stranded, nuclease resistant RNA oligonucleotide RISC inactivator between about 10-40 nucleotides in length, wherein the RISC inactivator comprises a nucleotide sequence sufficiently complementary to a guide strand sequence of the siRNA duplex to inhibit RNA silencing of the gene by the siRNA duplex, wherein the RISC inactivator comprises modified ribonucleotides, and wherein the RISC inactivator is a stochiometric, irreversible inhibitor of RISC function, such that RNA silencing of the gene is inhibited, wherein the RNA silencing is RNA interference.

2. The method of claim 1, wherein the RISC inactivator comprises between about 10-40 modified ribonucleotides.

3. The method of claim 1, wherein the RISC inactivator comprises between about 15-20 modified ribonucleotides.

4. The method of claim 1, wherein the RISC inactivator comprises between about 20-25 modified ribonucleotides.

5. The method of claim 1, wherein the RISC inactivator comprises between about 25-30 modified ribonucleotides.

6. The method of claim 1, wherein the RISC inactivator comprises between about 30-35 modified ribonucleotides.

7. The method of claim 1, wherein the RISC inactivator comprises between about 35-40 modified ribonucleotides.

8. The method of claim 1, wherein the RISC inactivator is administered at about 0.1-20nM doses.

9. The method of claim 1, wherein the RISC inactivator is administered at a dose of less than about 500 nM.

10. The method of any one of claims 1, 2 and 3-7, wherein the RISC inactivator 2'-O-methyl modified nucleotides.

11. The method of any one of claims 1, 2 and 3-7, wherein the RISC inactivator comprises locked nucleic acid (LNA) modifications.

12. The method of any one of claims 1, 2 and 3-7, wherein the RISC inactivator comprises phosphorothioate modifications.

13. The method of any one of claims 1, 2 and 3-9, wherein the RISC inactivator comprises a nucleotide sequence which is perfectly complementary to the guide strand of the siRNA duplex.

* * * * *

SEQUENCE LISTING

```
<160> NUMBER OF SEQ ID NOS: 15

<210> SEQ ID NO 1
<211> LENGTH: 31
<212> TYPE: RNA
<213> ORGANISM: Artificial Sequence
<220> FEATURE:
<223> OTHER INFORMATION: synthetic construct

<400> SEQUENCE: 1
caucacguac gcggaauacu ucgaaauguc c                                      31

<210> SEQ ID NO 2
<211> LENGTH: 31
<212> TYPE: RNA
<213> ORGANISM: Artificial Sequence
<220> FEATURE:
<223> OTHER INFORMATION: synthetic construct

<400> SEQUENCE: 2
caucacguac gcggaauacu ucgaaauguc c                                      31

<210> SEQ ID NO 3
<211> LENGTH: 31
<212> TYPE: RNA
<213> ORGANISM: Artificial Sequence
<220> FEATURE:
<223> OTHER INFORMATION: synthetic construct

<400> SEQUENCE: 3
ggacauuucg aaguauuccg cguacgugau g                                      31

<210> SEQ ID NO 4
<211> LENGTH: 31
<212> TYPE: RNA
<213> ORGANISM: Artificial Sequence
<220> FEATURE:
<223> OTHER INFORMATION: synthetic construct

<400> SEQUENCE: 4
```

```
acauuucgaa guauuccgcg uacgugaugu u                                        31

<210> SEQ ID NO 5
<211> LENGTH: 31
<212> TYPE: RNA
<213> ORGANISM: Artificial Sequence
<220> FEATURE:
<223> OTHER INFORMATION: synthetic construct

<400> SEQUENCE: 5
ucuucacuau acaaccuacu accucaaccu u                                        31

<210> SEQ ID NO 6
<211> LENGTH: 21
<212> TYPE: RNA
<213> ORGANISM: Artificial Sequence
<220> FEATURE:
<223> OTHER INFORMATION: synthetic construct

<400> SEQUENCE: 6
uauacaaccu acuaccucau u                                                   21

<210> SEQ ID NO 7
<211> LENGTH: 34
<212> TYPE: RNA
<213> ORGANISM: Artificial Sequence
<220> FEATURE:
<223> OTHER INFORMATION: synthetic construct

<400> SEQUENCE: 7
gaacaucacg uacgcggaau acuucgaaau gucc                                     34

<210> SEQ ID NO 8
<211> LENGTH: 21
<212> TYPE: RNA
<213> ORGANISM: Artificial Sequence
<220> FEATURE:
<223> OTHER INFORMATION: synthetic construct

<400> SEQUENCE: 8
ucgaaguauu ccgccuacgu g                                                   21

<210> SEQ ID NO 9
<211> LENGTH: 21
<212> TYPE: RNA
<213> ORGANISM: Artificial Sequence
<220> FEATURE:
<223> OTHER INFORMATION: synthetic construct

<400> SEQUENCE: 9
cguacgcgga auacuucgaa a                                                   21

<210> SEQ ID NO 10
<211> LENGTH: 34
<212> TYPE: RNA
<213> ORGANISM: Artificial Sequence
<220> FEATURE:
<223> OTHER INFORMATION: synthetic construct

<400> SEQUENCE: 10
ggacauuucg aaguauuccg cguacgugau guuc                                     34

<210> SEQ ID NO 11
<211> LENGTH: 36
<212> TYPE: RNA
<213> ORGANISM: Artificial Sequence
<220> FEATURE:
```

```
<223> OTHER INFORMATION: synthetic construct

<400> SEQUENCE: 11
gugaacauca cguacgcgga auacuucgaa augucc                                36

<210> SEQ ID NO 12
<211> LENGTH: 40
<212> TYPE: RNA
<213> ORGANISM: Artificial Sequence
<220> FEATURE:
<223> OTHER INFORMATION: synthetic construct

<400> SEQUENCE: 12
ggacauuucg aaguauuccg cguacgugau guucaccucg                            40

<210> SEQ ID NO 13
<211> LENGTH: 21
<212> TYPE: RNA
<213> ORGANISM: Artificial Sequence
<220> FEATURE:
<223> OTHER INFORMATION: synthetic construct

<400> SEQUENCE: 13
uguacgcgga auacuucgaa a                                                21

<210> SEQ ID NO 14
<211> LENGTH: 40
<212> TYPE: RNA
<213> ORGANISM: Artificial Sequence
<220> FEATURE:
<223> OTHER INFORMATION: synthetic construct

<400> SEQUENCE: 14
ucuucacuau acaaccuacu accucaaccu uuuauacaac                            40

<210> SEQ ID NO 15
<211> LENGTH: 21
<212> TYPE: RNA
<213> ORGANISM: Artificial Sequence
<220> FEATURE:
<223> OTHER INFORMATION: synthetic construct

<400> SEQUENCE: 15
ugagguagua gguuguauag u                                                21
```